US012005254B2

United States Patent
Melman

(10) Patent No.: US 12,005,254 B2
(45) Date of Patent: Jun. 11, 2024

(54) ELECTRICAL FIELD USAGE IN COCHLEAS

(71) Applicant: COCHLEAR LIMITED, New South Wales (AU)

(72) Inventor: Ryan Orin Melman, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 743 days.

(21) Appl. No.: 16/980,498

(22) PCT Filed: Mar. 12, 2019

(86) PCT No.: PCT/IB2019/051992
§ 371 (c)(1),
(2) Date: Sep. 14, 2020

(87) PCT Pub. No.: WO2019/175764
PCT Pub. Date: Sep. 19, 2019

(65) Prior Publication Data
US 2021/0023371 A1 Jan. 28, 2021

Related U.S. Application Data

(60) Provisional application No. 62/642,566, filed on Mar. 13, 2018.

(51) Int. Cl.
*A61N 1/36* (2006.01)
*A61N 1/05* (2006.01)
*H04R 25/00* (2006.01)

(52) U.S. Cl.
CPC ....... *A61N 1/36039* (2017.08); *A61N 1/0541* (2013.01); *A61N 1/36038* (2017.08); *H04R 25/30* (2013.01); *H04R 2225/025* (2013.01)

(58) Field of Classification Search
CPC .............. A61N 1/36039; A61N 1/0541; A61N 1/36038; H04R 25/30; H04R 2225/025
See application file for complete search history.

(56) References Cited

U.S. PATENT DOCUMENTS 8,532,781 B1 9/2013 Vanpoucke
2007/0270949 A1 11/2007 Paolini et al.
(Continued)

FOREIGN PATENT DOCUMENTS

CN 105934219 A 9/2016
CN 106105267 A 11/2016
(Continued)

OTHER PUBLICATIONS

Office Action for China Patent Application No. 2019800189372, mailed Mar. 31, 2021.
(Continued)

*Primary Examiner* — Joseph M Dietrich
(74) *Attorney, Agent, or Firm* — Pilloff Passino & Cosenza LLP; Martin J. Cosenza

(57) ABSTRACT

A method including causing current to flow from a first electrode of an intra-cochlea electrode array to a second electrode of the intra-cochlea electrode array at a plurality of temporal locations, measuring, at a third electrode and a fourth electrode of the intra-cochlea electrode array, a voltage induced by the flowing current at the plurality of temporal locations and determining that a change between the voltage measurements at the third electrode and the fourth electrode has occurred from the first temporal location to the second temporal location.

20 Claims, 34 Drawing Sheets

(56) References Cited

U.S. PATENT DOCUMENTS

| | | |
|---|---|---|
| 2009/0023976 A1 | 1/2009 | Cho et al. |
| 2009/0248110 A1 | 10/2009 | Choi et al. |
| 2011/0087085 A1 | 4/2011 | Tsampazis et al. |
| 2012/0071957 A1 | 3/2012 | Carter |
| 2012/0316454 A1 | 12/2012 | Carter |
| 2015/0112408 A1 | 4/2015 | Kals |
| 2015/0126900 A1 | 5/2015 | Walraevens et al. |
| 2015/0258337 A1 | 9/2015 | Long et al. |
| 2015/0314122 A1 | 11/2015 | Kabot et al. |
| 2016/0015291 A1 | 1/2016 | Tsampazis et al. |
| 2016/0059014 A1 | 3/2016 | Johnston et al. |
| 2016/0059015 A1 | 3/2016 | Risi et al. |
| 2018/0056058 A1 | 3/2018 | Heasman et al. |
| 2018/0169399 A1 | 6/2018 | Housley et al. |
| 2018/0280687 A1 | 10/2018 | Carter et al. |

FOREIGN PATENT DOCUMENTS

| | | |
|---|---|---|
| CN | 106232175 A | 12/2016 |
| CN | 107708796 A | 2/2018 |
| EP | 1754509 A1 | 2/2007 |
| KR | 100859979 B1 | 9/2008 |
| WO | 2009121108 A1 | 10/2009 |
| WO | 2018173010 A1 | 9/2018 |

OTHER PUBLICATIONS

International Search Report & Written Opinion for PCT/IB2019/051992, mailed Jul. 9, 2019.

Phillip Tran et al., "Development of Heather for Cochlear Implant Stimulation Using a New Modeling Workflow," IEEE Transactions on Biomedical Engineering, Oct. 22, 2014, pp. 728-735, vol. 62, issue 2.

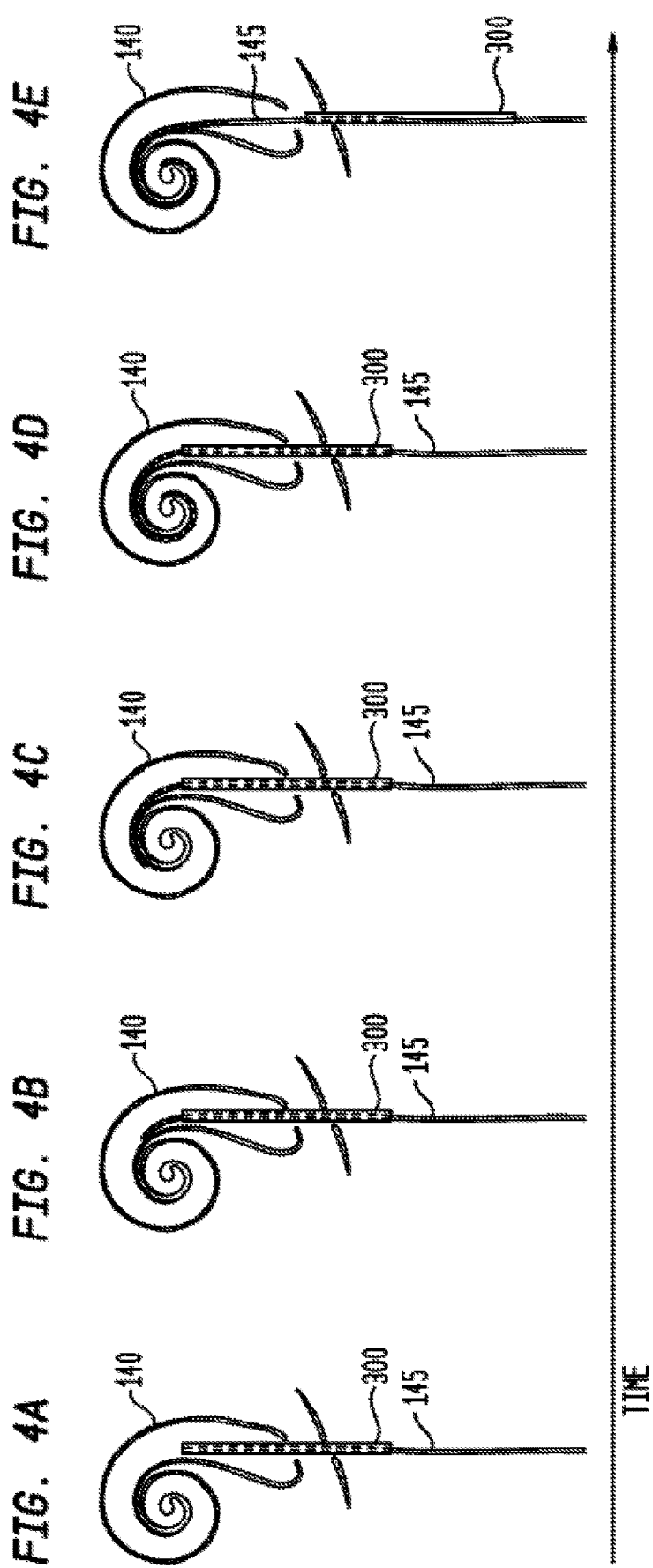

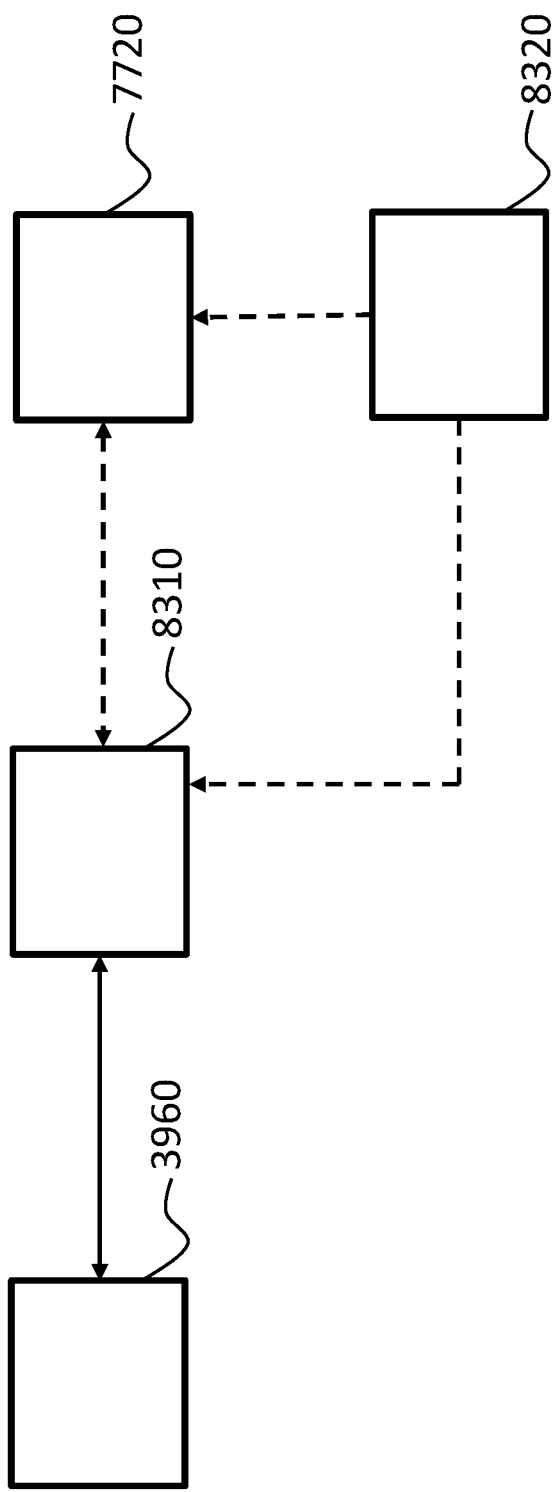

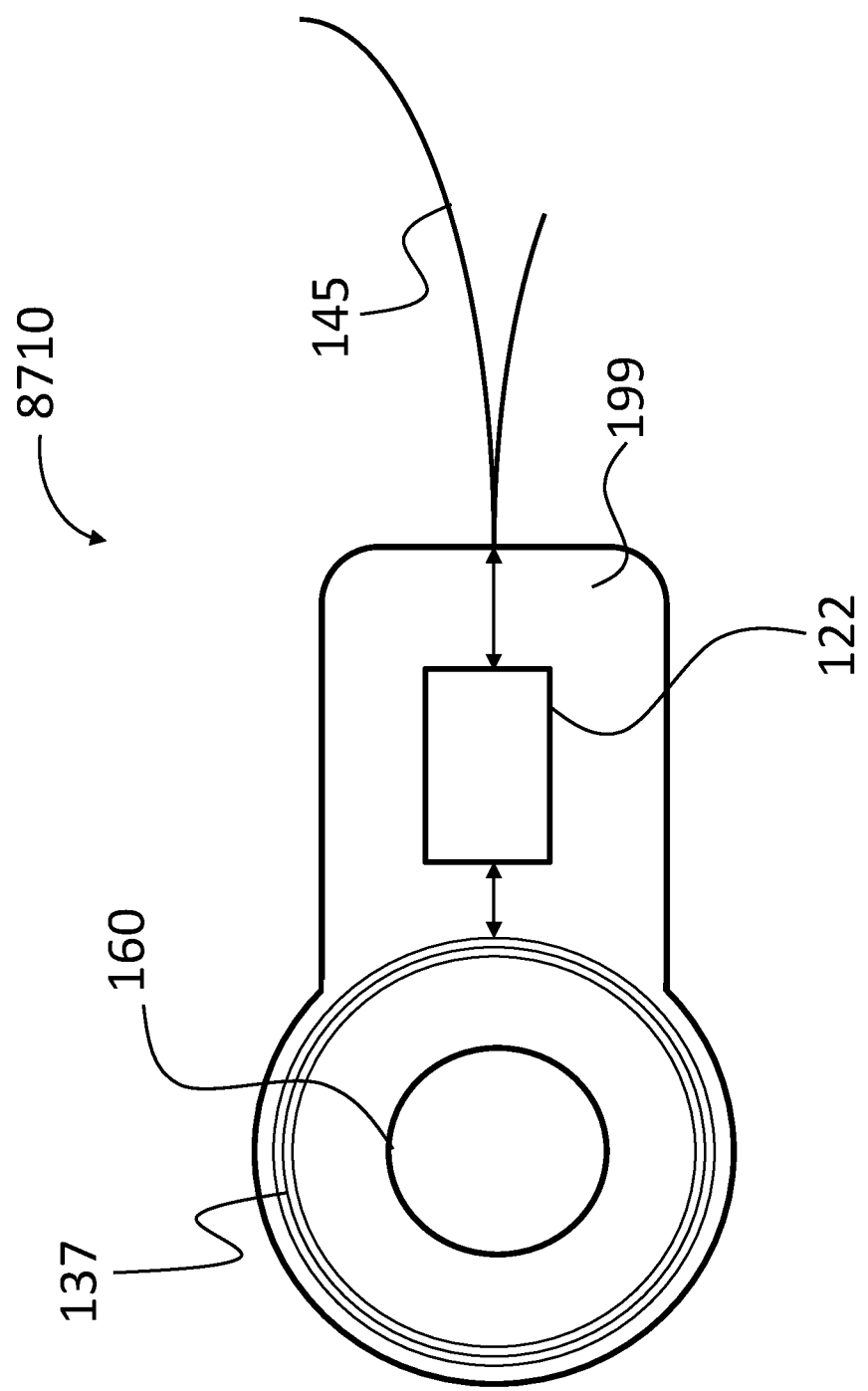

ELECTRICAL FIELD USAGE IN COCHLEAS

CROSS-REFERENCE TO RELATED APPLICATIONS

This application claims priority to U.S. Provisional Application No. 62/642,566, entitled ELECTRICAL FIELD USAGE IN COCHLEAS, filed on Mar. 13, 2018, naming Ryan Orin MELMAN of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. A hearing prosthesis can be a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting.

SUMMARY

In accordance with an exemplary embodiment, there is a method, comprising causing current to flow from a first electrode of an intra-cochlea electrode array to a second electrode of the intra-cochlea electrode array at a plurality of temporal locations, measuring, at a third electrode and a fourth electrode of the intra-cochlea electrode array, a voltage induced by the flowing current at the plurality of temporal locations, and determining that a change in a difference between the voltage measurements at the third electrode and the fourth electrode has occurred from the first temporal location to the second temporal location.

In another exemplary embodiment, there is a method, comprising measuring a voltage, induced by an electric field, at a plurality of intra-cochlea electrodes located in a cochlea, wherein the voltages are measured relative to a common reference electrode separate from the plurality of intra-cochlea electrodes where the measurements are taken, monitoring the relative magnitude of the measured voltages over time, and detecting a voltage change across the plurality of intra-cochlea electrodes based on the monitored relative magnitude that is representative of a voltage change at the reference electrode.

In another embodiment, there is a method, comprising generating an electric field within a cochlea of a recipient utilizing a cochlear implant, measuring a voltage with the cochlear implant, induced by the electric field, at two intra-cochlea measurement electrodes that are part of the cochlear implant, wherein respective voltages are measured relative to a common reference electrode and the measurement electrodes are spaced symmetrically about the reference electrode, and identifying the presence of an asymmetry in the voltage measurements.

In another exemplary embodiment, there is a system, comprising a cochlear implant sub-system including an electrode array and a control sub-system, wherein the system is configured to:
    operate electrodes of the electrode array as a source and a sink;
    operate electrodes of the electrode array as read electrodes; and
    enable communication between the control sub-system and the cochlear implant sub-system, and
the control sub-system is configured to evaluate signals from the cochlear implant sub-system to identify the existence of an asymmetrical electrical field about the electrode array.

BRIEF DESCRIPTION OF THE DRAWINGS

Embodiments are described below with reference to the attached drawings, in which:

FIGS. 4A-4E are simplified side views depicting the position and orientation of a cochlear implant electrode assembly insertion guide tube relative to the cochlea at each of a series of successive moments during an exemplary implantation of the electrode assembly into the cochlea;

FIGS. 5-9 are exemplary system components of an exemplary embodiment;

DETAILED DESCRIPTION

Figure 1A:
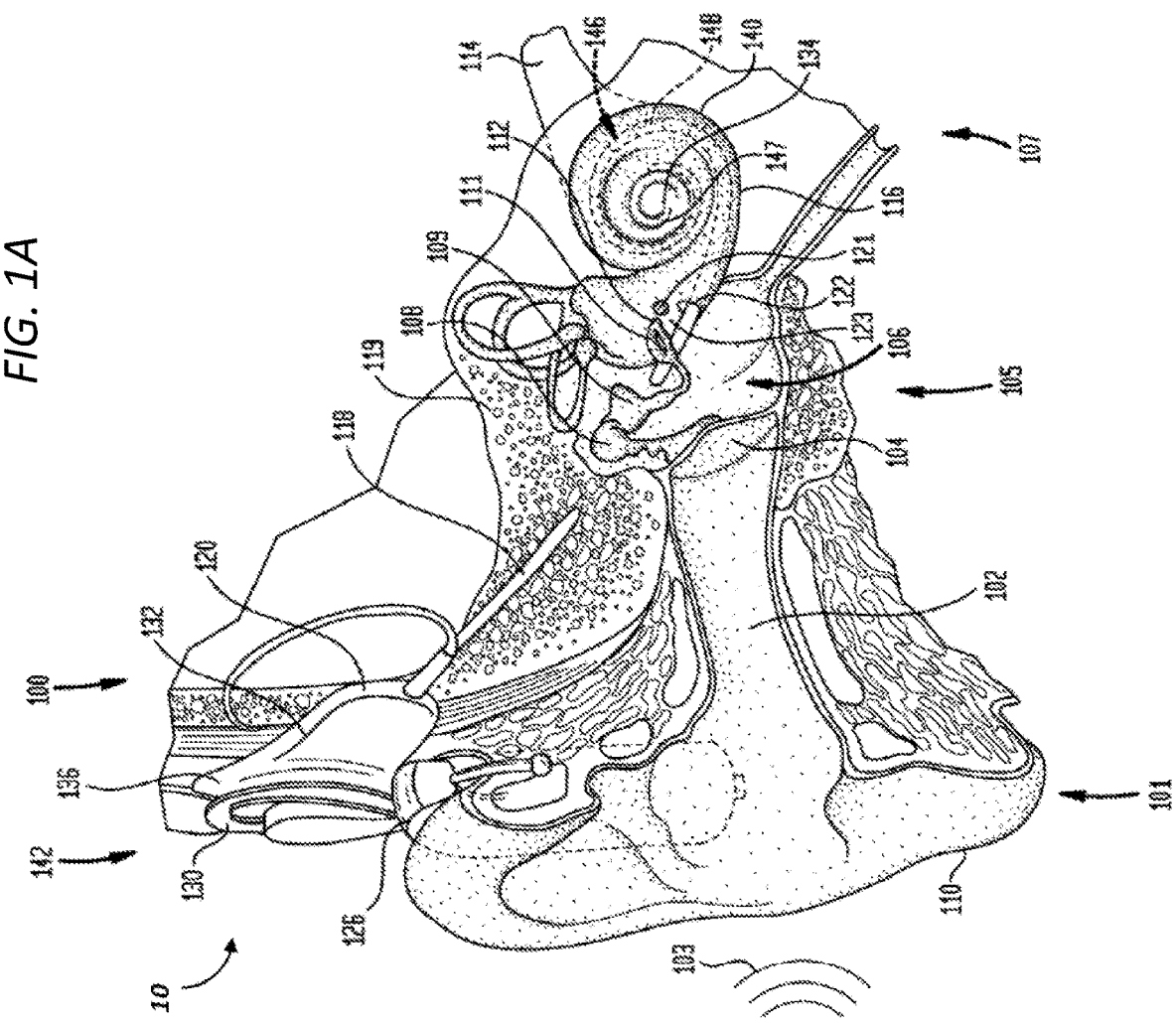
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. Additionally, it is noted that the teachings detailed herein are also applicable to other types of hearing prostheses, such as by way of example only and not by way of limitation, bone conduction devices (percutaneous, active transcutaneous and/or passive transcutaneous), direct acoustic cochlear stimulators, middle ear implants, and conventional hearing aids, etc. Indeed, it is noted that the teachings detailed herein are also applicable to so-called multi-mode devices. In an exemplary embodiment, these multi-mode devices apply both electrical stimulation and acoustic stimulation to the recipient. In an exemplary embodiment, these multi-mode devices evoke a hearing percept via electrical hearing and bone conduction hearing. Accordingly, any disclosure herein with regard to one of these types of hearing prostheses corresponds to a disclosure of another of these types of hearing prostheses or any medical device for that matter, unless otherwise specified, or unless the disclosure thereof is incompatible with a given device based on the current state of technology. Thus, the teachings detailed herein are applicable, in at least some embodiments, to partially implantable and/or totally implantable medical devices that provide a wide range of therapeutic benefits to recipients, patients, or other users, including hearing implants having an implanted microphone, auditory brain stimulators, pacemakers, visual prostheses (e.g., bionic eyes), sensors, drug delivery systems, defibrillators, functional electrical stimulation devices, etc.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances when there are no natural hearing capabilities, for example, due to degeneration of previous natural hearing capability or to the lack of any natural hearing capability, for example, from birth). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities and to recipients having no natural vision capabilities). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired, or indeed never existed.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is rechargeable via the transcutaneous link.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1B:
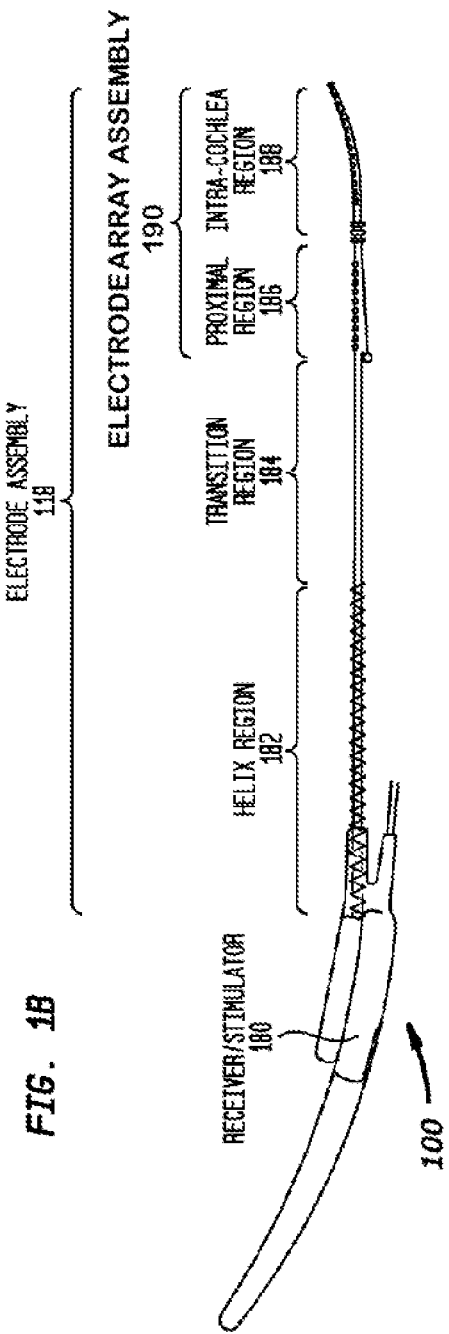
FIG. 1B depicts a side view of the cochlear implant 100 outside of the recipient.

FIG. 1B is a side view of a cochlear implant 100 without the other components of system 10 (e.g., the external components). Cochlear implant 100 comprises a receiver/stimulator 180 and an electrode assembly or lead 118. Electrode assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity sub-section of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Electrode array 146 may be inserted into cochlea 140 with the use of an insertion guide. It is noted that while the embodiments detailed herein are described in terms of utilizing an insertion guide or other type of tool to guide the array into the cochlea, in some alternate insertion embodiments, a tool is not utilized. Instead, the surgeon utilizes his or her fingertips or the like to insert the electrode array into the cochlea. That said, in some embodiments, alternate types of tools can be utilized other than and/or in addition to insertion guides. By way of example only and not by way of limitation, surgical tweezers like can be utilized. Any device, system, and/or method of inserting the electrode array into the cochlea can be utilized according to at least some exemplary embodiments.

The teachings detailed herein are directed towards identifying phenomenon inside a cochlea. Some embodiments can include utilizing imaging (e.g., CT scan, X-ray, etc.), which require the patient to be exposed to radiation during the process of obtaining medical images, as well as the need for medical equipment in the operating room to provide and otherwise obtain the imaging, as well as a subsequent analysis by an expert to assess the correct insertion of the electrode holder. Some embodiments of the teachings detailed herein utilize such, while other embodiments specifically do not utilize such, but instead utilize other methods to evaluate or otherwise obtain information indicative of a given electrode array insertion scenario. Some embodiments include the action of measuring neuronal activation after stimulation. This exemplary embodiment can require subjective expert analysis and/or can also be dependent on having a good/acceptable neural response. However, in some instances, such is not always obtainable. Again, as with the aforementioned imaging, some embodiments herein utilize such while other embodiments specifically do not utilize such methods. In at least some exemplary embodiments, methods of determining an insertion scenario can utilize voltage measurements in the cochlea. In an exemplary embodiment of such embodiments, the interpretation of the obtained voltage measurements still requires subjective analysis by an expert. In addition, these measurements can be rendered more difficult to interpret than otherwise might be the case by the presence of so-called air bubbles, open electrodes, shorted electrodes, and/or electrode extrusion. Some embodiments of the teachings detailed herein utilize the aforementioned voltage measurements coupled with expert analysis, while in other embodiments some of the teachings detailed herein specifically avoid utilization of expert analysis to obtain or otherwise analyze and electrode array insertion scenario.

Some embodiments include obtaining voltage measurements from inside and/or outside the cochlea and analyzing them in, by way of example only and not by way of limitation, an automated manner, by comparing the voltage measurements to statistical data.

Figure 2A:
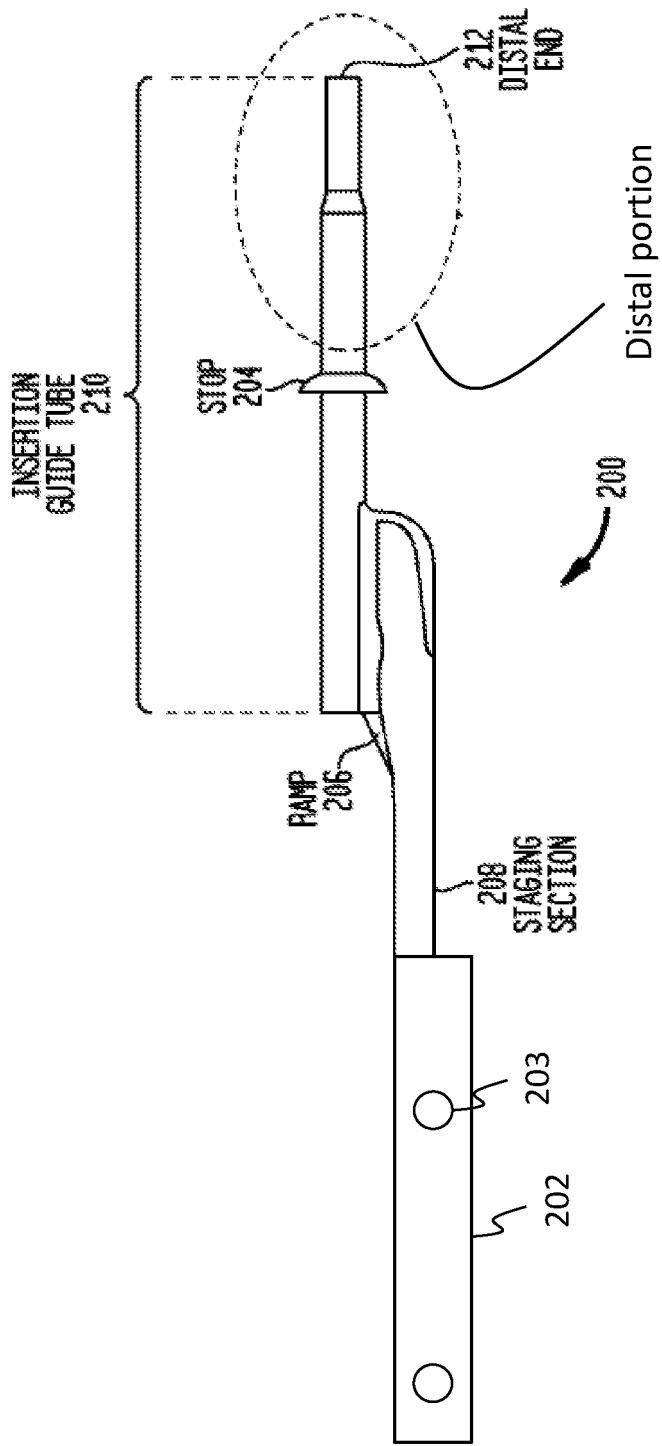
FIGS. 2A and 2B are side views of an embodiment of an insertion guide for implanting a cochlear implant electrode assembly such as the electrode assembly illustrated in FIG. 1.

FIG. 2A presents a side view of an embodiment of an insertion guide for implanting an elongate electrode assembly generally represented by electrode assembly 145 (corresponding to assembly 190 of FIG. 1B) into a mammalian cochlea, represented by cochlea 140. The illustrative insertion guide, referred to herein as insertion guide 200, includes an elongate insertion guide tube 210 configured to be inserted into cochlea 140 and having a distal end 212 from which an electrode assembly is deployed. Insertion guide tube 210 has a radially-extending stop 204 that may be utilized to determine or otherwise control the depth to which insertion guide tube 210 is inserted into cochlea 140.

Insertion guide tube 210 is mounted on a distal region of an elongate staging section 208 on which the electrode assembly is positioned prior to implantation. A robotic arm adapter 202 is mounted to a proximal end of staging section 208 to facilitate attachment of the guide to a robot, which adapter includes through holes 203 through which bolts can be passed so as to bolt the guide 200 to a robotic arm, as will be detailed below. During use, electrode assembly 145 is advanced from staging section 208 to insertion guide tube 210 via ramp 206. After insertion guide tube 210 is inserted to the appropriate depth in cochlea 140, electrode assembly 145 is advanced through the guide tube to exit distal end 212 as described further below.

Figure 2B:
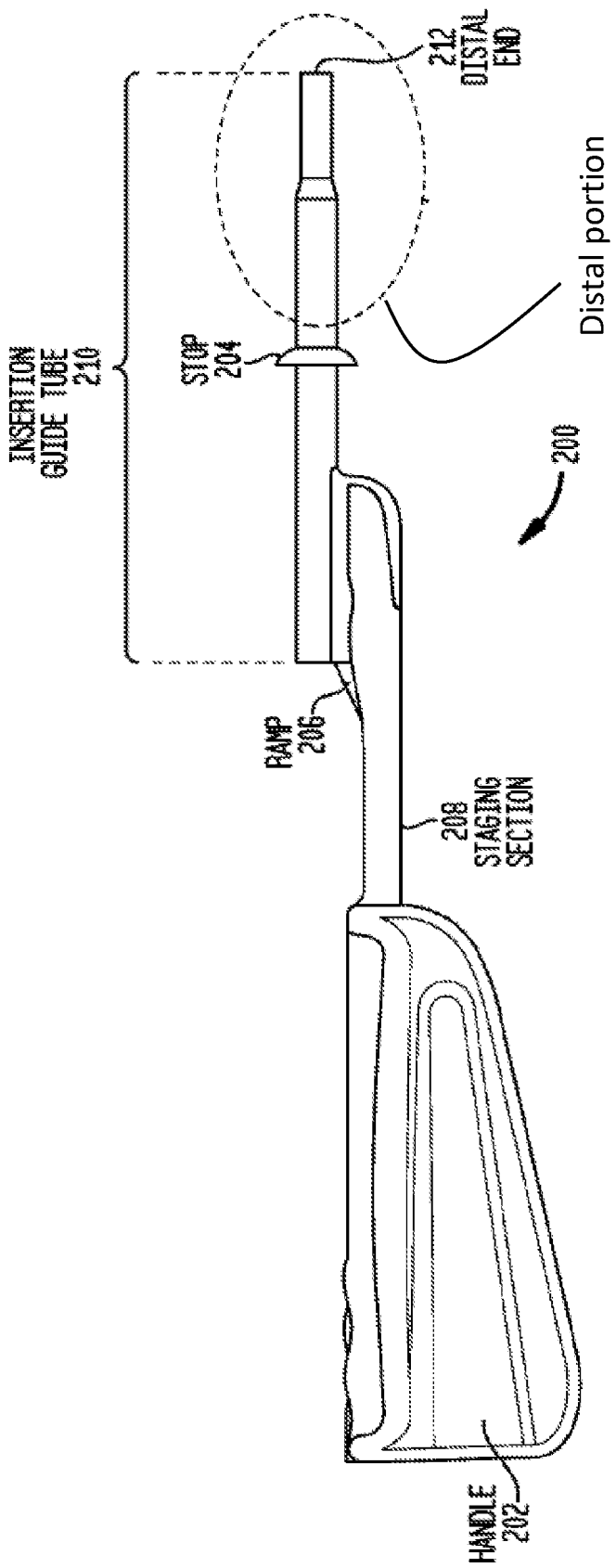

FIG. 2B depicts an alternate embodiment of the insertion guide 200, that includes a handle 202 that is ergonomically designed to be held by a surgeon. This in lieu of the robotic arm adapter 202.

Figure 3A:
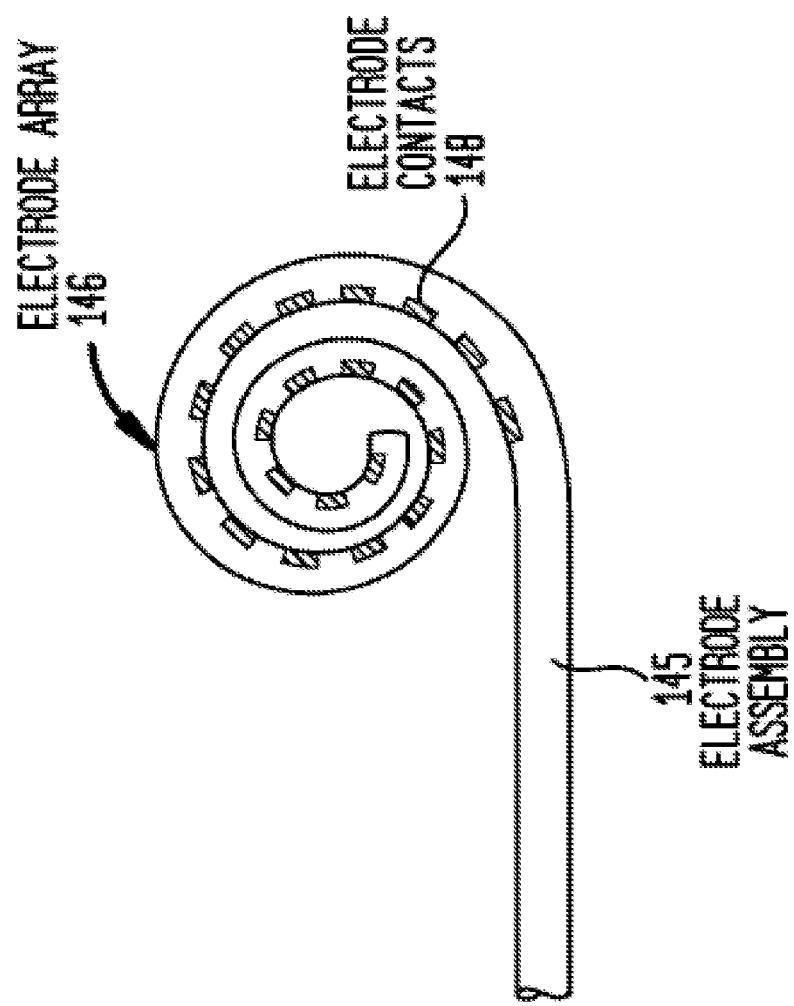
FIGS. 3A and 3B are side and perspective views of an electrode assembly extended out of an embodiment of an insertion sheath of the insertion guide illustrated in FIG. 2.
Figure 3B:
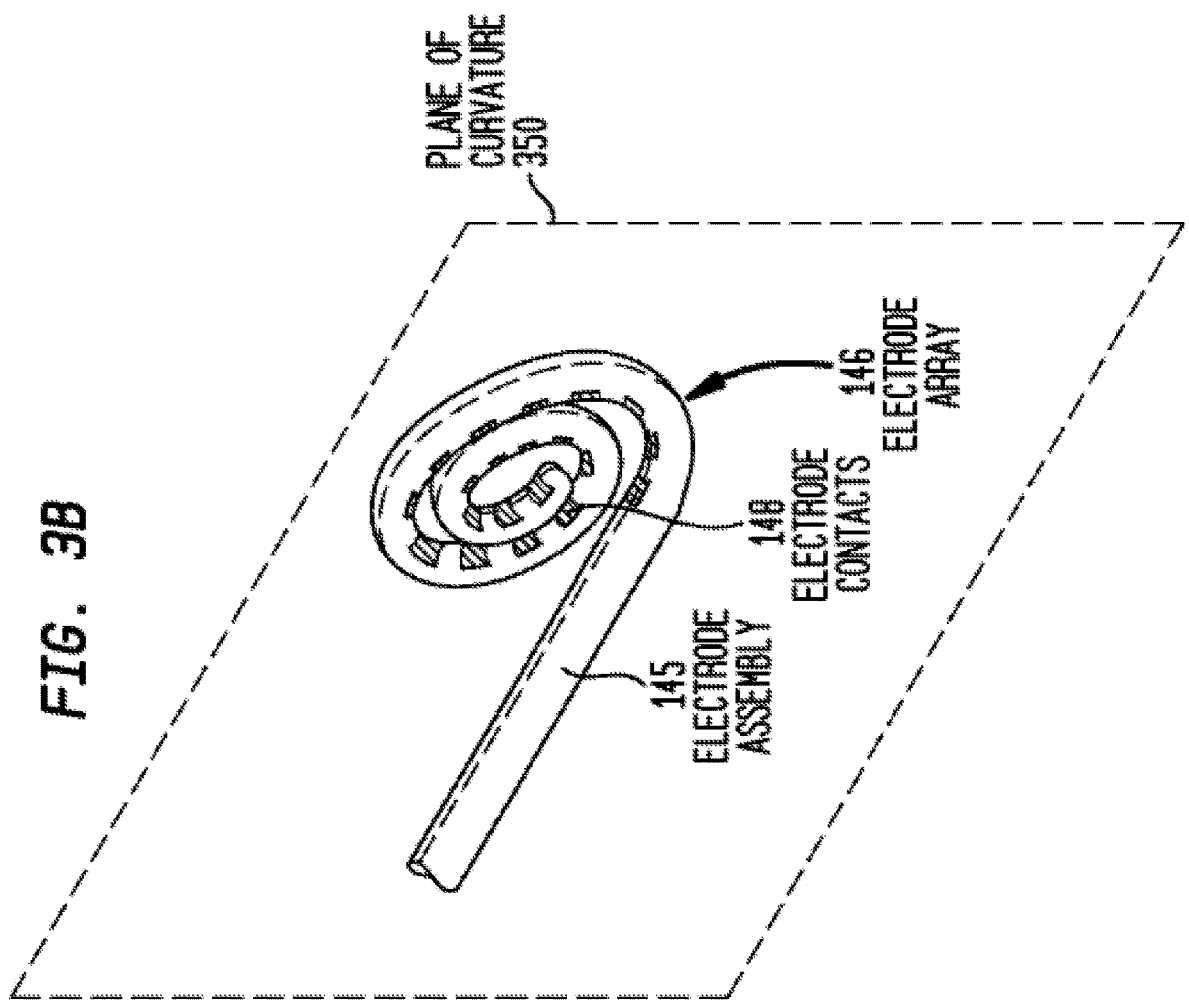

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that embodiments of the insertion guides detailed herein and/or variations thereof can be applicable to a so-called straight electrode array, which electrode array does not curl after being free of a stylet or insertion guide tube, etc., but instead remains straight.

FIGS. 4A-4E are a series of side-views showing consecutive exemplary events that occur in an exemplary implantation of electrode assembly 145 into cochlea 140. Initially, electrode assembly 145 and insertion guide tube 310 are assembled. For example, electrode assembly 145 is inserted (slidingly or otherwise) into a lumen of insertion guide tube 300. The combined arrangement is then inserted to a predetermined depth into cochlea 140, as illustrated in FIG. 4A. Typically, such an introduction to cochlea 140 is achieved via cochleostomy 122 (FIG. 1) or through round window 121 or oval window 112. In the exemplary implantation shown in FIG. 4A, the combined arrangement of electrode assembly 145 and insertion guide tube 300 is inserted to approximately the first turn of cochlea 140.

As shown in FIG. 4A, the combined arrangement of insertion guide tube 300 and electrode assembly 145 is substantially straight. This is due in part to the rigidity of insertion guide tube 300 relative to the bias force applied to the interior wall of the guide tube by pre-curved electrode assembly 145. This prevents insertion guide tube 300 from bending or curving in response to forces applied by electrode assembly 145, thus enabling the electrode assembly to be held straight, as will be detailed below.

As noted, electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. This induces stress in electrode assembly 145. Pre-curved electrode assembly 145 will tend to twist in insertion guide tube 300 to reduce the induced stress. In the embodiment configured to be implanted in scala tympani of the cochlea, electrode assembly 145 is pre-curved to have a radius of curvature that approximates the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Conventional insertion guide tubes typically have a lumen dimensioned to allow the entire tapered electrode assembly to travel through the guide tube. Because the guide tube is able to receive the relatively larger proximal region of the electrode assembly, there will be a gap between the relatively smaller distal region of the electrode assembly and the guide tube lumen wall. Such a gap allows the distal region of the electrode assembly to curve slightly until the assembly can no longer curve due to the lumen wall.

Returning to FIGS. 3A-3B, perimodiolar electrode assembly 145 is pre-curved in a direction that results in electrode contacts 148 being located on the interior of the curved assembly, as this causes the electrode contacts to face the modiolus when the electrode assembly is implanted in or adjacent to cochlea 140. Insertion guide tube 300 retains electrode assembly 145 in a substantially straight configuration, thereby preventing the assembly from taking on the configuration shown in FIG. 3B.

It is noted that while the embodiments above disclose the utilization of an insertion tool, in some other embodiments, insertion of the electrode array is not executed utilizing an insertion tool. Moreover, in some embodiments, when in insertion tool is utilized, the insertion tool is not as intrusive as that detailed in the figures. In an exemplary embodiment, there is no distal portion of the tool. That is, the insertion tool stops at the location where the distal portion begins. In an exemplary embodiment, the tool stops at stop 204. In this regard, there is little to no intrusion of the tool into the cochlea. Any device, system and/or method that can enable the insertion of the electrode array can be utilized in at least some exemplary embodiments.

As can be recognized from the above, the electrode array can be utilized to obtain the data utilized in the methods herein, such as by way of example only and not by way of limitation, the voltages at the read electrodes, and can also be used to provide the stimulating electrode (just in case for some reason that was not clear). FIG. 5 depicts an exemplary system for utilizing the cochlear implant to obtain such information. Presented in functional terms, there is a test unit 3960 in signal communication with unit 8310, which in turn is in signal communication, optionally with a unit 7720 and a unit 8320, the details of which will be described below.

Unit 3960 can correspond to an implantable component of an electrode array, as seen in FIG. 1. More specifically, FIG. 6 depicts an exemplary high-level diagram of a receiver/stimulator 8710 (the implantable portion of 100) of a cochlear implant, looking downward. As can be seen, the receiver/stimulator 8710 includes a magnet 160 that is surrounded by a coil 137 that is in two-way communication (although in other embodiments, the communication is one-way) with a stimulator unit 122, which in turn is in communication with the electrode array 145. Receiver/stimulator 8710 further includes a cochlear stimulator unit 122, in signal communication with the coil 137. The coil 137 and the stimulator unit 122 are encased in silicon as represented by element 199. In an exemplary embodiment, receiver/stimulator 8710 is utilized as test unit 3960, and is used to acquire information about electrode array position.

Figure 8:
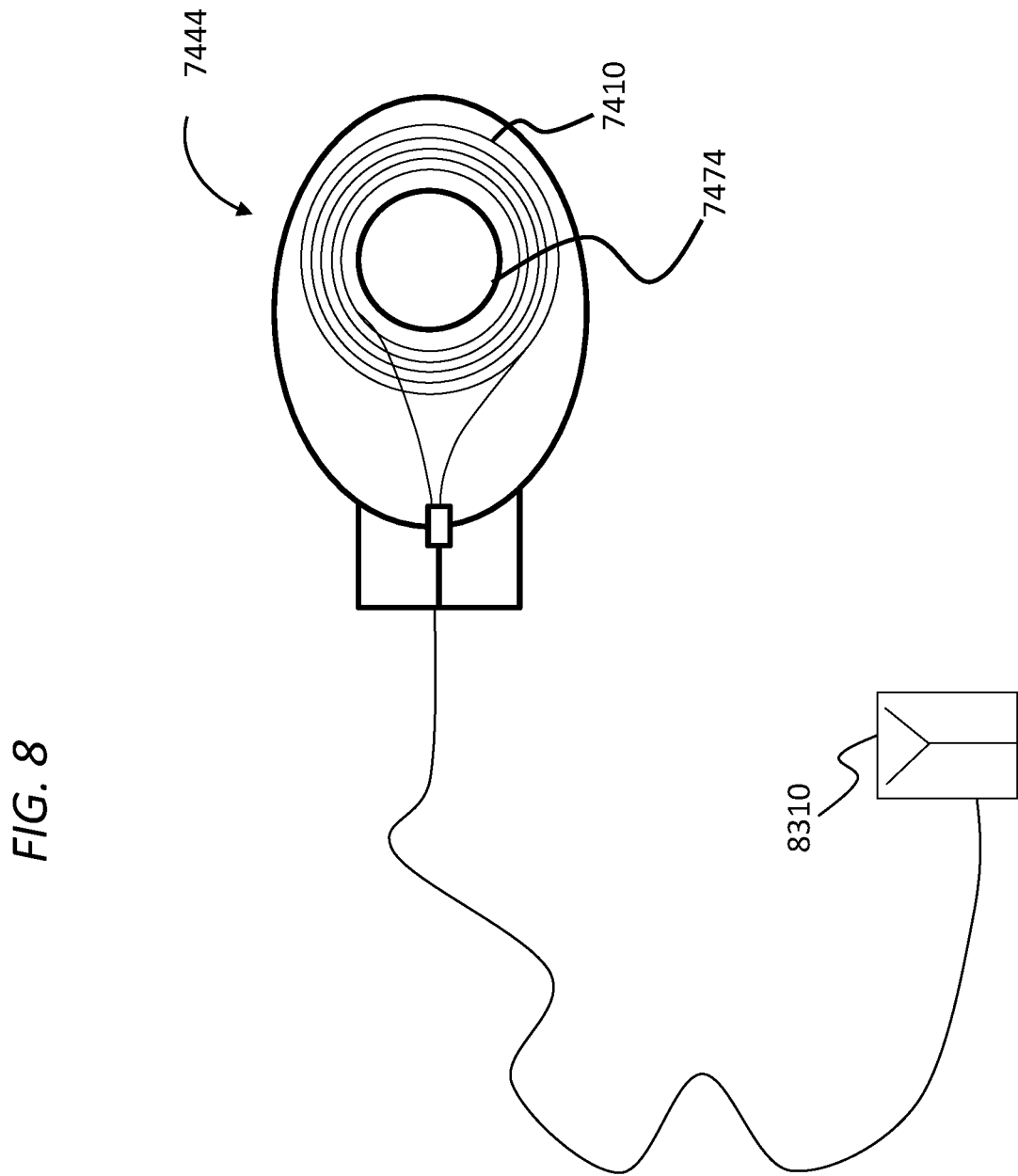

FIG. 8 depicts an exemplary RS (receiver/stimulator) interface 7444 which is presented by way of concept. An inductance coil 7410 is configured to establish a magnetic inductance field so as to communicate with the corresponding coil of the receiver-stimulator of the cochlear implant. Interface 7444 includes a magnet 7474 so as to hold the inductance coil 7410 against the coil of the receiver/stimulator of the cochlear implant in a manner analogous to how the external component of the cochlear implant is held against the implanted component, and how the coils of those respective components are aligned with one another. As can be seen, an electrical lead extends from the coil 7410 to control unit 8310, representing signal communication between interface 7444, and control unit 8310.

Figure 9:
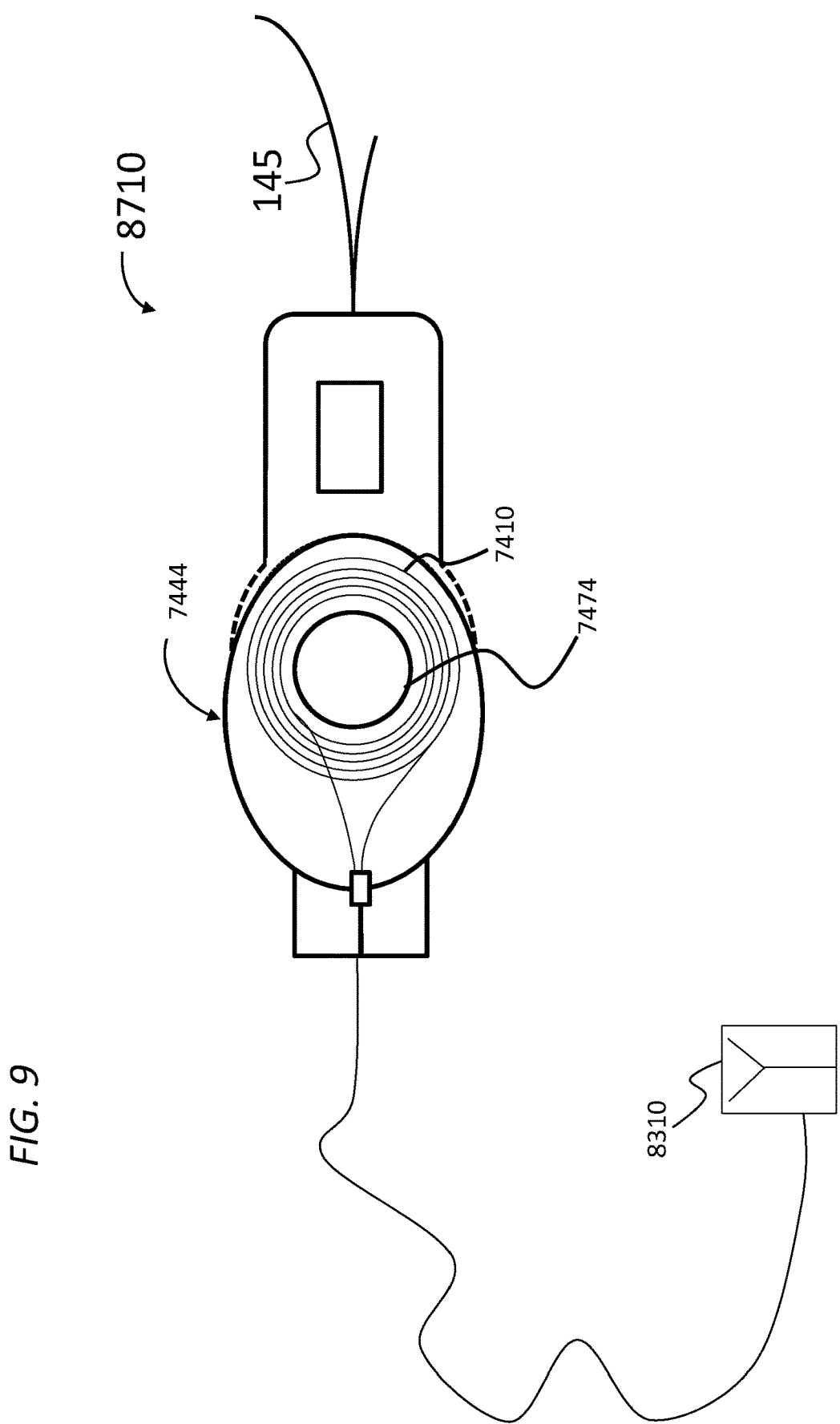

FIG. 9 depicts an exemplary embodiment of the receiver/stimulator 8710 in signal communication with the control unit 8310 via electrical lead that extends from the interface device 7444 having coil 7410 about a magnet 7474 as can be seen. The interface device 7444 communicates via an inductance field with the inductance coil of the receiver/stimulator 8710 so that the data acquired by the implantable component 8710 (receiver/stimulator) can be transferred to the control unit 8310.

Note also that in at least some alternate exemplary embodiments, control unit 8310 can communicate with the so-called "hard ball" reference electrode of the implantable component of the cochlear implant so as to enable communication of data from the receiver/stimulator 8710 to control unit 8310 and/or vice versa.

It is noted that in the embodiment of FIG. 9, control unit 8310 is in signal communication with the various other components as detailed herein, which components are not depicted in FIG. 9 for purposes of clarity.

Also functionally depicted in FIG. 5 is the optional embodiment where an electrode array insertion robotic system/actuator system 7720 and an input device 8320 is included in the system. In an exemplary embodiment, the input device 8320 could be a trigger of a hand held device that controls the actuator system 7720 and can stop and/or start insertion of the actuator. In an exemplary embodiment, the input device 8320 could be a trigger on the tool 8200.

Figure 7:
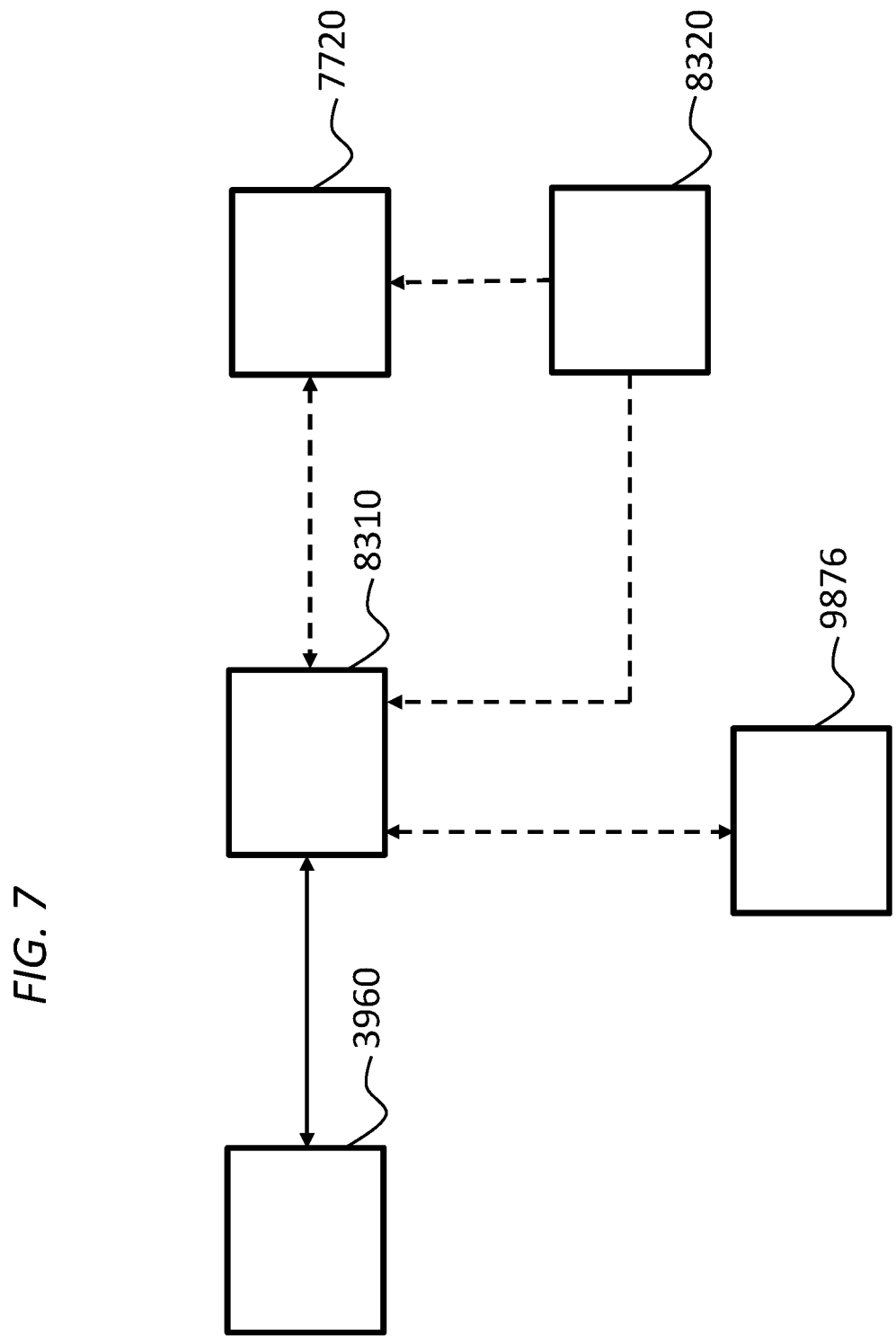

Control unit 8310 can be a signal processor or the like, or a personal computer or the like, or a mainframe computer or the like, etc., that is configured to receive signals from the test unit 3960 and analyze those signals to evaluate the data obtained (it can also be used to control the implant/control the application of current). More particularly, the control unit 8310 can be configured with software or the like to analyze the signals from test unit 3960 in real time and/or in near real time as the electrode array is being advanced into the cochlea by actuator assembly 7720 (if present, and if not present, while the array is being inserted/advanced by hand). The control unit 8310 analyzes the input from test unit 3960, after partial and/or full implantation and/or after the surgery is completed and/or as the electrode array advanced by the actuator assembly 7720 and/or as the electrode array is advanced by the surgeon by hand. The controller/control unit can be programmed to also control the stimulation/control the providing of current to the electrodes during the aforementioned events/situations. The controller 8310 can evaluate the input to determine if there exists a phenomenon according to the teachings detailed herein. That said, in an alternate embodiment, as depicted in FIG. 7, or in addition to this, the controller 8310 can output a signal to an optional monitor 9876 or other output device (e.g., buzzer, light, etc.), that can provide the surgeon or other healthcare professional performing the operation or evaluating the data postoperatively, etc., indicative of the data obtained and/or indicative of a conclusion reached by the control unit 8310. Note also that in an exemplary embodiment, the control unit 8310 can be a dumb unit in the sense that it simply passes along signals to the implant (e.g., the control unit can instead be a series of, for example, buttons where a surgeon depression is one button to provide stimulation to a given electrode).

Still, in some embodiments, the control unit 8310 is configured or otherwise programmed to evaluate input and determine if the input indicates that the electrode array is positioned in a given manner were otherwise that the electrode array is positioned in a manner different than that which was desired. In an exemplary embodiment, upon such a determination, control unit 8310 could halt the advancement of the array into the cochlea by stopping the actuator(s) of actuator assembly 7720 and/or could slow the actuator(s) so as to slow rate of advancement of the electrode array into the cochlea and/or could reverse the actuator(s) so as to reverse or otherwise retract the electrode array within the cochlea (either partially or fully). Alternatively, in embodiments where actuator assembly 7720 is not present, control unit 8310 could provide an indication to the surgeon or the like (via an integrated component, such as a buzzer or a light on the control unit, or an LDC screen, or via device 9876) to halt and/or slow the insertion, etc. In at least some exemplary embodiments, control unit 8310 can be configured to override the input from input unit 8320 input by the surgeon or the user.

Some exemplary embodiments utilize the receiver/stimulator 8710 as a test unit 3910 that enables the action of obtaining the data and the action of providing current to the electrode, and/or any one or more of the method actions detailed herein. In an exemplary embodiment, the receiver/stimulator 8710 and/or control unit 3810 and/or actuator assembly 7720 and/or input device 8320 are variously utilized to execute one or more or all of the method actions detailed herein, alone or in combination with an external component of a cochlear implant, and/or with the interface 7444, which can be used after the receiver/stimulator 8710 is fully implanted in the recipient and the incision to implant such has been closed (e.g., days, weeks, months or years after the initial implantation surgery). The interface 7444 can be used to control the receiver/stimulator to execute at least some of the method actions detailed herein (while in some other embodiments, the receiver/stimulator can execute such in an autonomous or semi-autonomous manner, without being in communication with an external component) and/or can be used to obtain data from the receiver/stimulator after execution of such method actions.

Some exemplary utilizations of the embodiments of FIGS. 5-9 will now be described, along with some modifications thereto.

Without being bound by theory, in a homogenous medium such as perilymph in a cochlea, an electric field from a point charge, such as an electrode of a cochlear electrode array (a simplification for the purposes of discussion—in reality, electrodes are a distributed source in view of the scales at issue here—the use of a point charge is a simplification that enables the description of a charge distribution in a simple manner/without 3 dimensional equations), will disperse equally in all directions, spherically. As the volume of a sphere increases with the cube of the radius, the electric field diminishes inversely with the cube of the radius. The voltage generated by the electric field can be calculated as the first derivative of the electric field. That is, the voltage measured across two points in an electric field can be determined by the difference in the electric field density. When a dipole is created from two equal and opposite point charges (such as in a scenario of utilizing one of the electrodes of the electrode array as a source and another of the electrodes of the electrode array as a sink, as distinct from utilizing, for example, the extra cochlear electrode is a sink), the resultant electric field is effectively the super-position of the two equal and opposite point charges. Thus the relationship of diminishing electric field with the cube of the distance still approximately holds.

Figure 10:
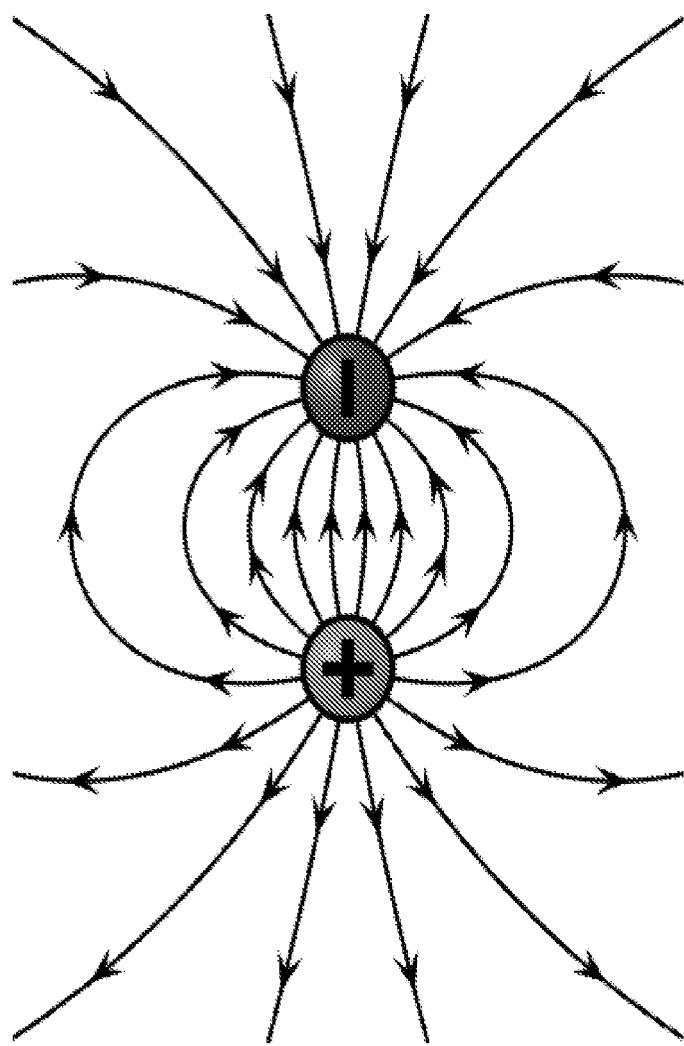
FIGS. 10-12 conceptually represent phenomenon associated with some embodiments.

Bipolar stimulation of a cochlear implant, such as where two electrodes of the electrode array implanted in the cochlea or otherwise in the cochlea at the time that bipolar stimulation is executed are respectively utilized as the source and a sink, produces a dipole within the cochlea. Within the dipole, in at least some exemplary scenarios, most of the current flows approximately parallel within ±5× the separation of the stimulating electrodes as shown in FIG. 10. In an exemplary embodiment, more than 80, 81, 82, 83, 84, 85, 86, 87, 88, 89, 90, 91, 92, 93, 94, 95, 96, 97, 98, or 99% of the current flows approximately parallel within the ±5×. Indeed, in some exemplary embodiments, if voltage is measured starting at the negative charge to the positive charge, a monotonic voltage gradient will be achieved between the negative and positive poles, with an effective "zero" charge point located equidistant from each of the point charges.

Figure 11:
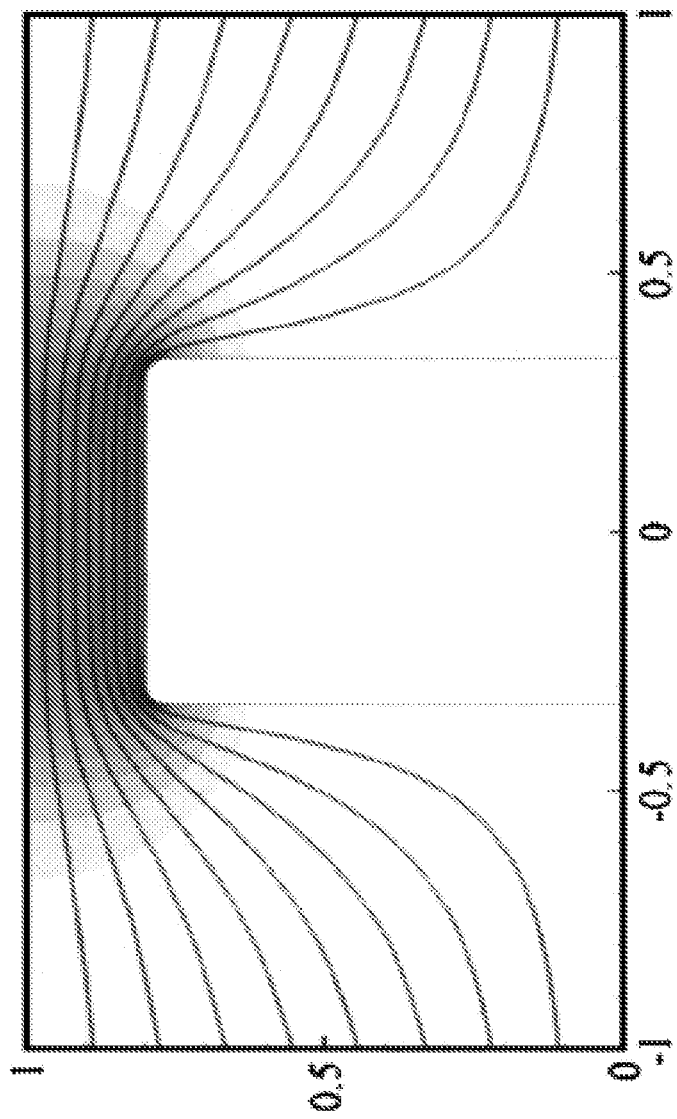
Figure 12:
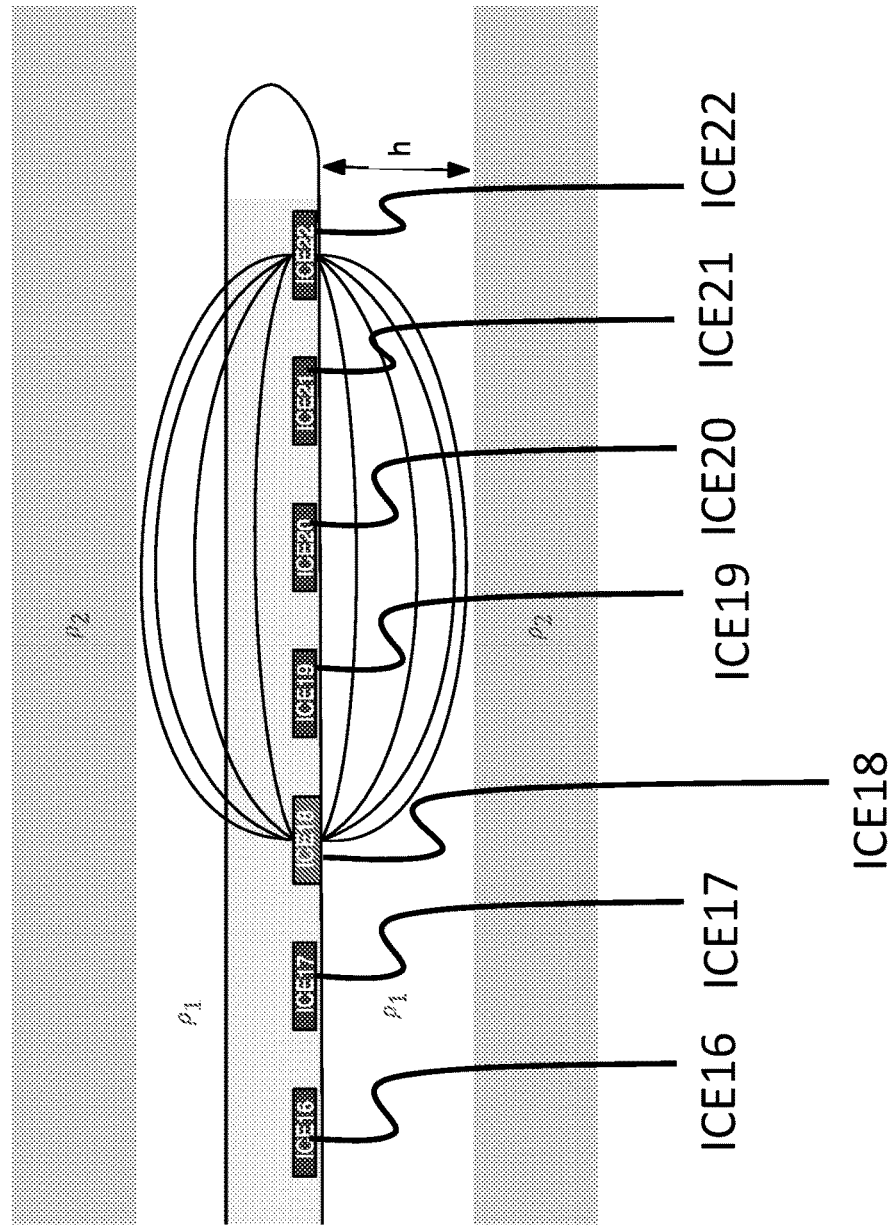

The quantity of current flowing out of a current source is at least effectively equal (including equal) to the current flowing back into the current source, in some embodiments where the source and sink are located in a cochlea with perilymph immersing both the source and a sink in a contiguous manner). By ensuring or otherwise utilizing current flow in the path of least impedance, the introduction of an insulator into a homogenous medium can cause an increase in current density at the boundary of the insulator as the current flows around that insulator. This can be seen in FIG. 10. Note that current Density (J), E-field (E) and impedance ($\rho$) are linked via Maxwell's equation $E=J\rho$. This is the case as the current density increases so does the E-field as shown in FIG. 11. In FIG. 11, the darker sections indicate current density, or more accurately, locations of higher current density relative to other locations.

Figure 13:
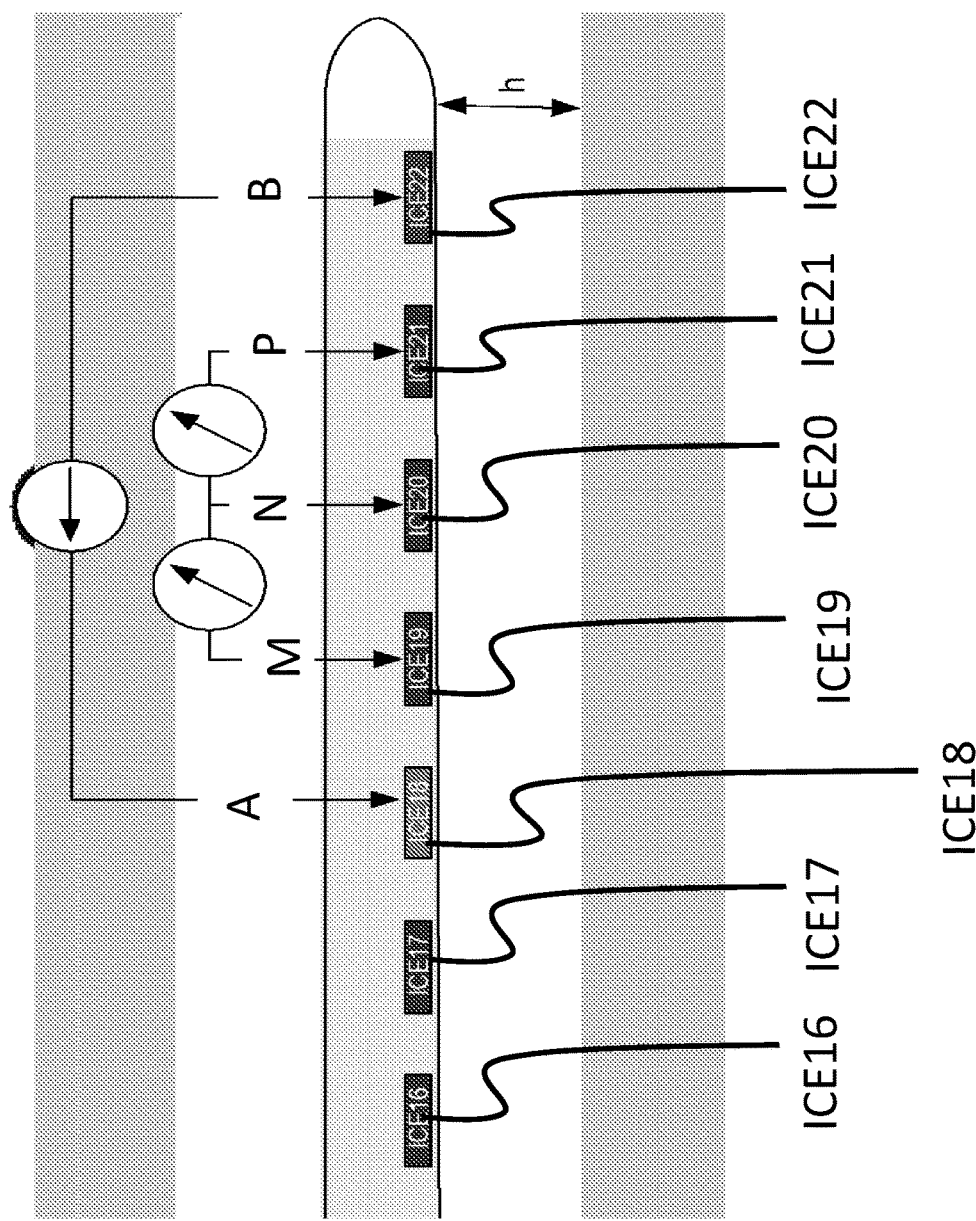
FIGS. 13 and 14 and 22 and 23 conceptually represent the usage of an electrode array according to some exemplary embodiments.

In at least some exemplary embodiments, the cochlear implant electrode array 146 provides stimulation to tissue utilizing a current source and sink established by two electrodes of the electrode array. In an exemplary embodiment, this current source provides sufficient current into tissue of the recipient to evoke a hearing percept. In some embodiments according to the teachings detailed herein, irrespective of whether or not a hearing percept is executed, although some embodiments apply a current that creates a field where no hearing percept is evoked and/or the threshold level at a given frequency for that recipient is higher than the current utilized, while in other embodiments, a hearing percept is evoked, the electrical field generated by the stimulating electrodes will radiate symmetrically until it encounters a wall, such as a wall of the cochlea, which is a high impedance structure, at least relative to the perilymph of the cochlea (e.g., 5, 10, 15, 20, 25, 30, 35, 40, 50, 75, 100 times, or more higher impedance than the perilymph). The high impedance interface will, in some embodiments, cause compression of the current as it preferentially flows through the perilymph, owing to the relative impedances, resulting in a further decrease in the electric field. In a radially symmetrical environment, such as the exemplary cylinder shown in FIG. 11, which can, in some embodiments, be treated as a cylinder of infinite length, the impact will be symmetrical. Thus if the voltage drop is measured between ICE20 (ICE being intra-cochlear electrode—as distinguished from an electrode that is not in the cochlea, at least not when the measurement is executed) and ICE21 (NP) as well as between ICE19 and ICE20 (MN), as is shown in FIG. 13, where electrodes 18 and 22 (ICE electrodes 18 and 22) are the stimulating electrodes (source and sink), in some exemplary scenarios, the electric field gradient would be identical, and thus the voltage measurements would be symmetrical for NP and MN. Additionally, in at least some exemplary scenarios, electrode ICE20 would be found to be located in a point of zero charge (providing that a constant electrode pitch is present, which, in some embodiments of the electrode array 146, is the case).

Figure 14:
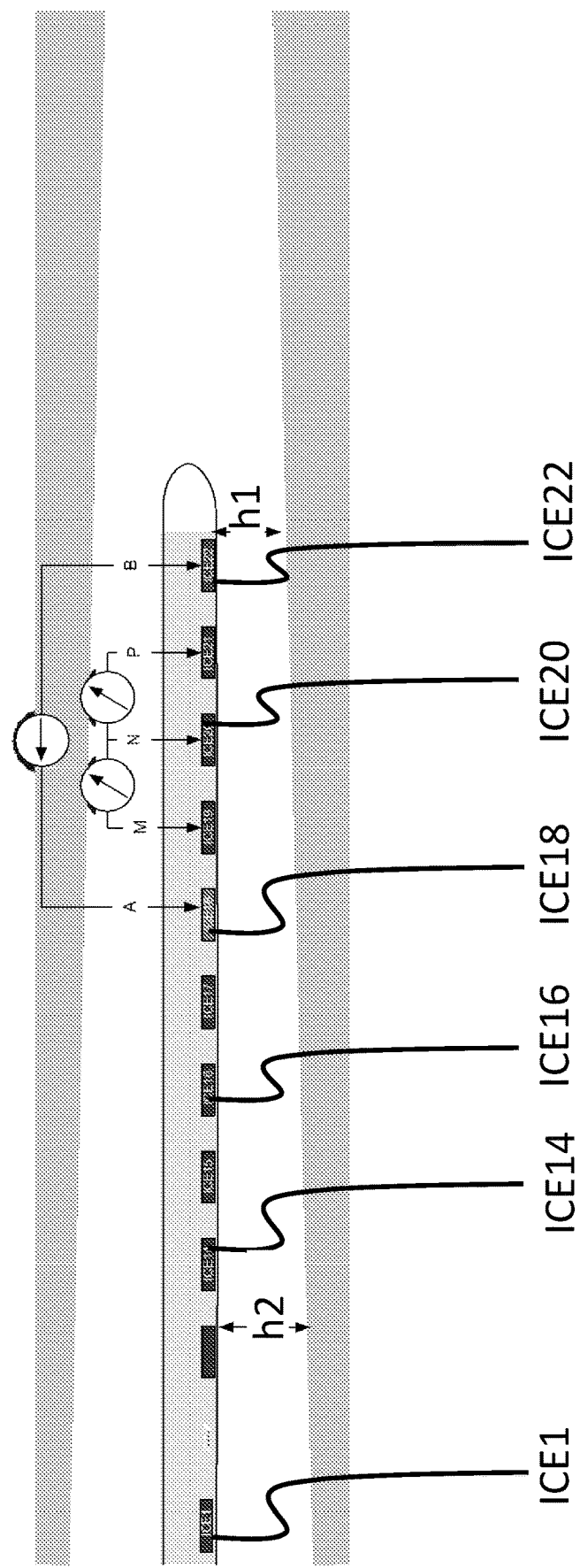

If the electrode is located in a tapering tube, as shown in FIG. 14, for example, if the current flowing between AB is constant, there will be, in some embodiments, a greater current density between measuring electrodes NP than between electrodes MN. This can be because there is less cross-sectional area of the low impedance current path at the apical end of the array. Thus, in some embodiments, the voltage drop between NP will be greater than for MN. Also, assuming a constant electrode pitch, in some embodiments, the null point will shift basally of electrode ICE20 due to the larger electric field at the apex.

FIGS. 13 and 14 present exemplary models of the cochlea with an electrode array therein. The variables h1 and h2 correspond to the distance/height of the electrodes above the wall of the cochlea.

Figure 15:
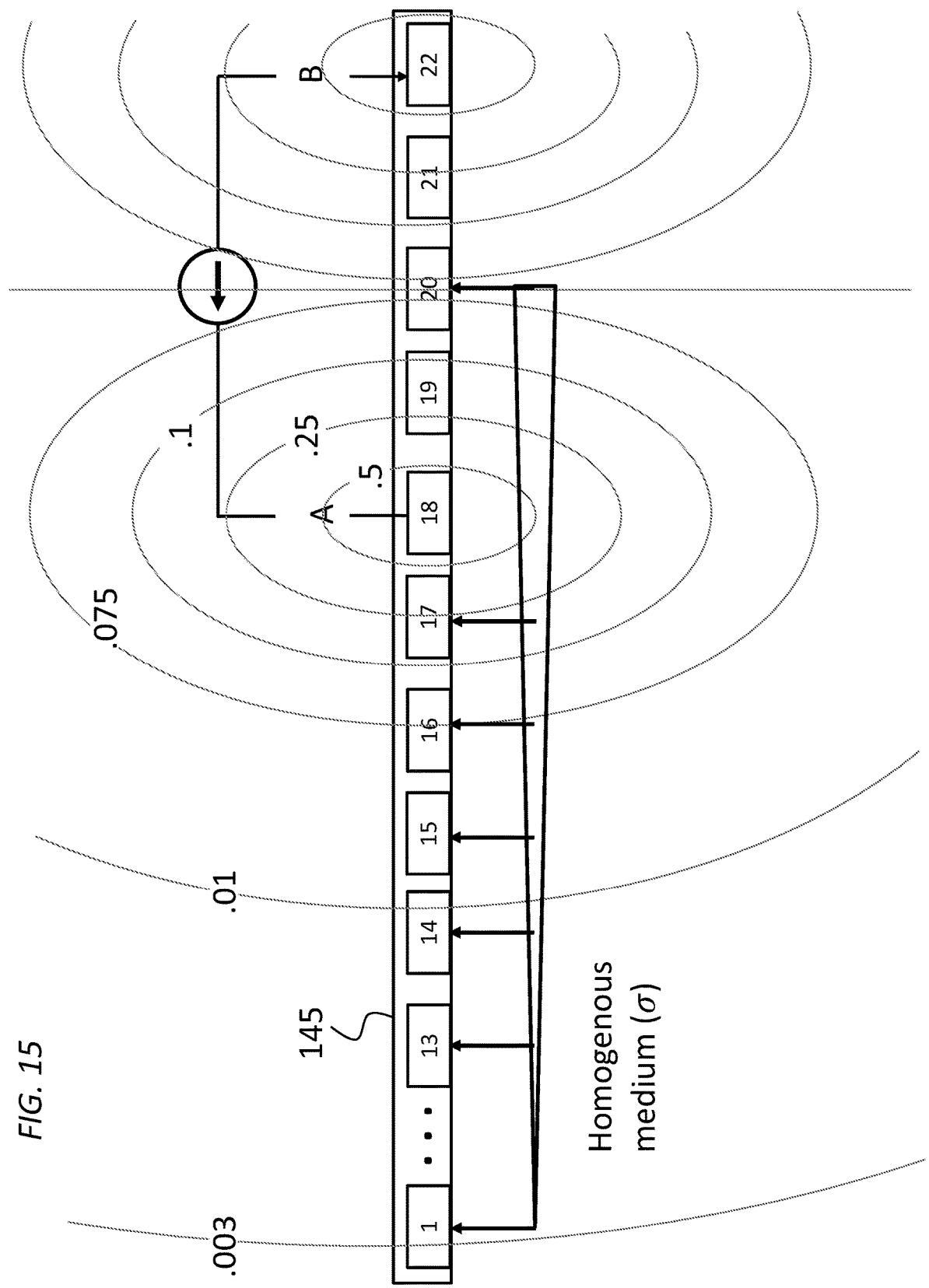
FIG. 15 conceptually represents electrical fields and the associated voltages read at certain electrodes.

FIG. 15 presents a conceptual diagram depicting the utilization of the electrodes basil of the basil most stimulating electrode (ICE 18) as read electrodes along with the utilization of electrode 20 as a read electrode. More specifically, electrode 20 is the reference electrode from which voltages for the other read electrodes are based. As is conceptually depicted by the elongated triangle, the further the read electrode from the reference electrode, the lower the voltage difference between the read electrode and the reference electrode. Superimposed on the electrodes of the electrode array of FIG. 15 are electric field curves. As can be seen, the electric fields are centered around the stimulating electrodes 18 and 22, where electrode 18 is utilized as the source and electrode 22 is utilized as the sink. It is noted that in an alternating current embodiment, the direction of current would be quickly reversed so that electrode 18 was the sink and electrode 22 was the source. This would occur at a frequency of 5, 10, 15, 20, 30, 40, 50, 75, 100 Hz or more.

In a homogeneous medium and in an infinite perfect cylinder, the null point would be exactly at electrode 20, as is depicted in FIG. 15. The electric field curves present voltage values.

In view of FIG. 15, it is to be understood that in at least some exemplary embodiments, there is a method that utilizes a dipole symmetrical about a reference electrode, where one or more or all of the non-stimulating electrodes are utilized as read electrodes, and the reference electrode is utilized as the reference voltage for the voltage readings at the other read electrodes. While the embodiment of FIG. 15 does not depict the utilization of electrodes 19 and 21 as read electrodes, in some alternate embodiments, these are also utilized as read electrodes.

In some embodiments, the electric field null position will also shift as the electrode position deviates from the axis of the tapering "tube," even in an infinite cylinder. In some embodiments, this can be because there will be a shift in the electric field concentration as the electrode(s) get closer to a high impedance interface then other electrode(s). In some embodiments, this can account for a baseline shift observed in some of the measurements, where ICE20 is used as a reference, as shown in FIG. 15. Any changes which compress the electrical field around the apical end of the array (such as a constriction or the apical electrode approaching a wall) will shift the null point of the dipole, making the reference electrode (ICE20) more positive. Conversely, any changes which "decompress" the electrical field around the apical and of the array (such as the electrode moving away from the wall) will shift the midpoint of the dipole, making the reference electrode less positive. It is to be understood than in at least some exemplary embodiments, the aforementioned changes with respect to the reference electrode will affect all of the other read electrodes in some exemplary embodiments. By way of example only and not by way of limitation, if the read electrode 20 becomes more positive, the values for electrodes 17, 16, 15, 14, 13 and so on will become less positive and/or will change by an equal amount (total amount or relative percentage).

Figure 16:
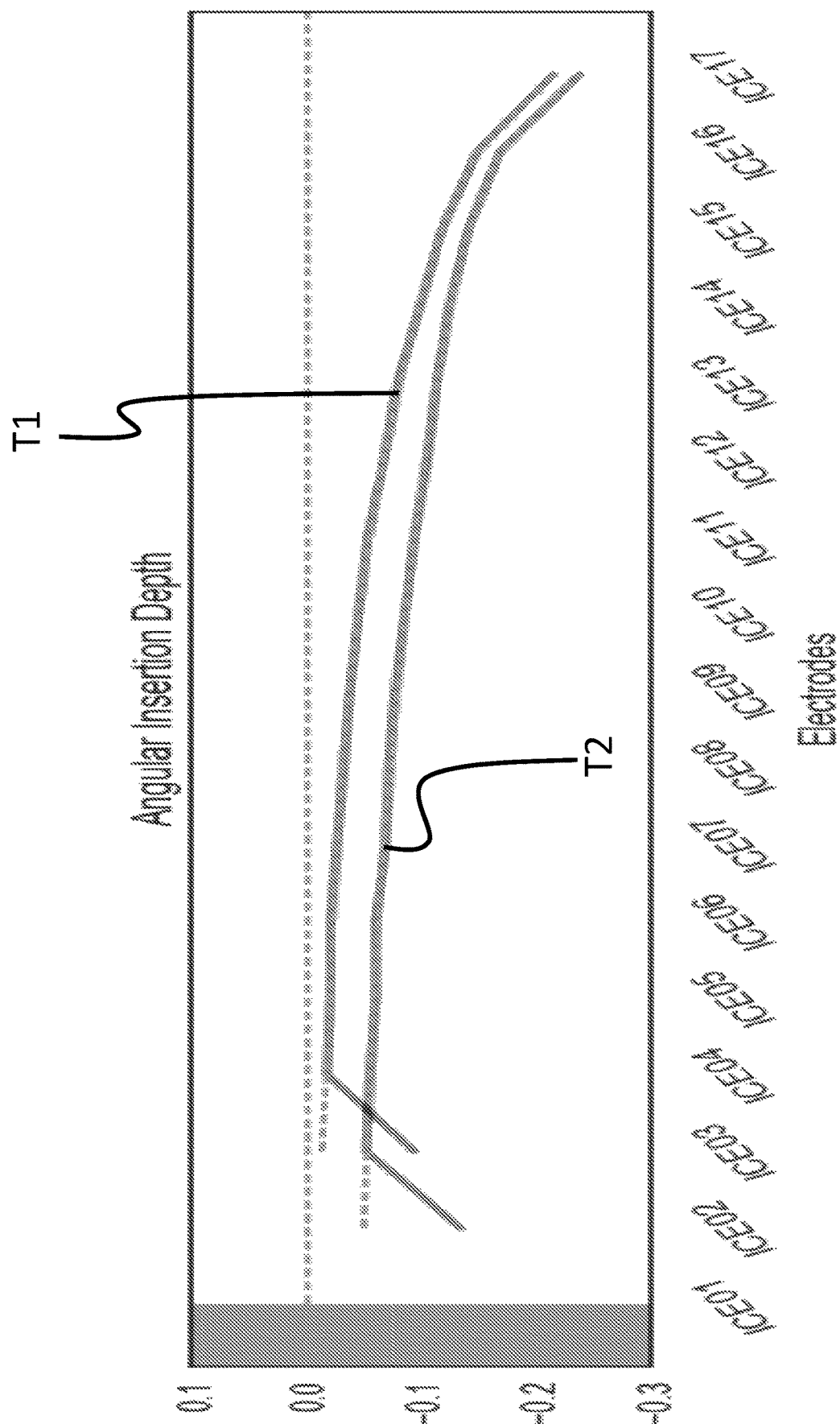
FIG. 16 presents an exemplary embodiment of a baseline shift in voltage readings according to an exemplary embodiment.

As the voltage on ICE20 becomes more positive, in some embodiments, it will cause all measurements performed with respect to ICE20 to appear to have a voltage reduction as shown in FIG. 16. In some embodiments, this rapid baseline shift, occurring over a very small insertion distance, is a consistent feature observed during the insertion of an electrode array into a human cochlea. In this regard, in FIG. 16 the baseline shift can be seen from the voltage curve that exists at time T1 versus the voltage curve that exists at time T2. Note that the curve for time T2 shows an extra value for an electrode that is not present in the curve for time T1. This is because, in this exemplary insertion scenario, between time T1 and T2, another electrode enters the cochlea due to advancement of the array.

In at least some exemplary embodiments, the aforementioned change in baseline voltage represented in FIG. 16 is a marker that is due to some anatomical feature, such as a constriction in the cochlea. In some embodiments, it is a marker related to the electrode dynamics during the insertion (such as, for example, one or more or all of the group comprising the stimulating electrodes plus the reference electrodes) coming into contact with the modiolus—in an exemplary embodiment, this can cause a centering of the dipole null. In either case, this biomarker is used in some embodiments as a highly consistent electrode position indicator that is created by a shift in the voltage on the reference electrode. In some embodiments, this shift is induced by a change in the balance of the electrical field of the stimulating electrode pair.

Figure 17:
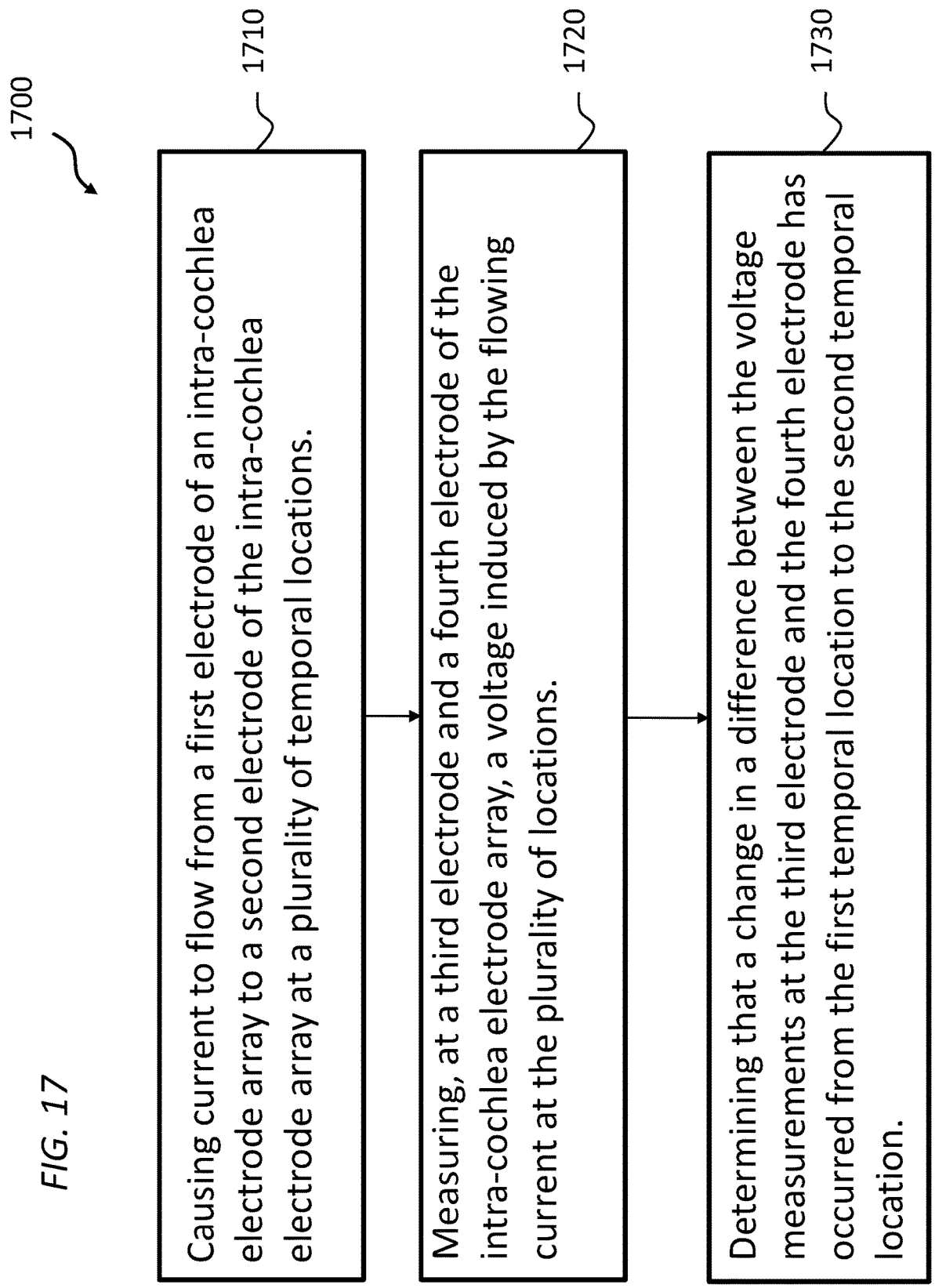
FIGS. 17-21 present some exemplary algorithms for some exemplary methods.

FIG. 17 presents an exemplary algorithm representing an exemplary method, method 1700. Method 1700 includes method action 1710, which includes causing current to flow from a first electrode of an intra-cochlea electrode array to a second electrode of the intra-cochlea electrode array at a plurality of temporal locations. By way of example only and not by way of limitation, this can be executed utilizing system 8710 detailed above, where the implantable portion of the cochlear implant 100 in general, and the electrode array 145 in particular, is utilized as the electrode array. The plurality of temporal location can correspond to a first temporal location where the electrode array is inserted a first distance into the cochlea, and a second temporal location after the first temporal location where the electrode array is inserted a second distance into the cochlea greater than the first instance. In an exemplary embodiment, these plurality of temporal locations can correspond to 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 80, 90, 100 or more temporal locations or any number of temporal locations therebetween and/or any range therebetween in one integer increments (e.g., 33, 44, 25-62, etc.). In an exemplary embodiment, the number of temporal locations can correspond to any integer between 1 and 10,000. In an exemplary embodiment, the first electrode can be electrode 22 and the second electrode can be electrode 18, consistent with the teachings detailed above. Alternatively, in an exemplary embodiment, the first and second electrodes can be electrodes 19 and 22. Of course, more distal electrodes can be utilized. Any set of electrodes that can enable the teachings detailed herein can be utilized in at least some exemplary embodiments.

Method 1700 also includes method action 1720, which includes measuring, at a third electrode and a fourth electrode of the intra-cochlea electrode array, a voltage induced by the flowing current at the plurality of temporal locations. In an exemplary embodiment, the third electrode and the fourth electrode can be, for example, any of the read electrodes herein, such as electrode 19 and electrode 21. In an exemplary embodiment, method action 1720 can be executed utilizing the system 8710 detailed above. Method 1700 also includes method action 1730, which includes determining that a change in a difference between the voltage measurements at the third electrode and the fourth electrode has occurred from the first temporal period to the second temporal period (note that this does not require a different to be determined, only that a change in the difference has occurred—this can be determined by determining that the quotient has changed, which can correspond to a difference—note that in an embodiment, any change, whether such be a change in a difference or a quotient, etc., can trigger this determination). This can be executed by the system of FIG. 5 detailed above. Additional details of this will be described in greater detail below. In an exemplary embodiment, method action 1730 is executed automatically by the system of FIG. 5. In an exemplary embodiment, method action 1730 is executed by, for example, presenting the voltage curve of FIG. 16 on a computer monitor or the like for each of the temporal locations. This can entail refreshing the view/image for each temporal location. When the curve changes/moves as a result of the aforementioned baseline shift, the surgeon can determine that the change in the difference between the voltage measurements has occurred. In an exemplary embodiment, the display will display the curves for a plurality of temporal locations for a given period of time. For example, the curves for the last five temporal locations may be displayed. Where the curves are the same, the curves will be presented one over top of each other. When the curve changes, the viewer will notice the change because there will be a new curve that is spatially separate from the prior curves.

Still, it is noted that in at least some exemplary embodiments, method 1700 is executed by only presenting data for the electrodes utilized in method action 1720 and/or is executed by only analyzing the data for those electrodes.

It is noted that the action of determining that a change in a difference between the voltage measurements at the third and fourth electrodes can include actually subtracting the two voltages from one another to obtain the difference or looking at the change in voltages at the individual electrodes between the temporal periods of time, and determining that a change in the difference has occurred without necessarily subtracting the two values from each other. Indeed, in some embodiments, no mathematical operation is executed. Instead, as noted above, the curves of the voltage measurements can be eyeballed. Any device, system, and/or method that can enable the determination that a change in a difference between the voltage measurements has occurred can be utilized in at least some exemplary embodiments.

Figure 18:
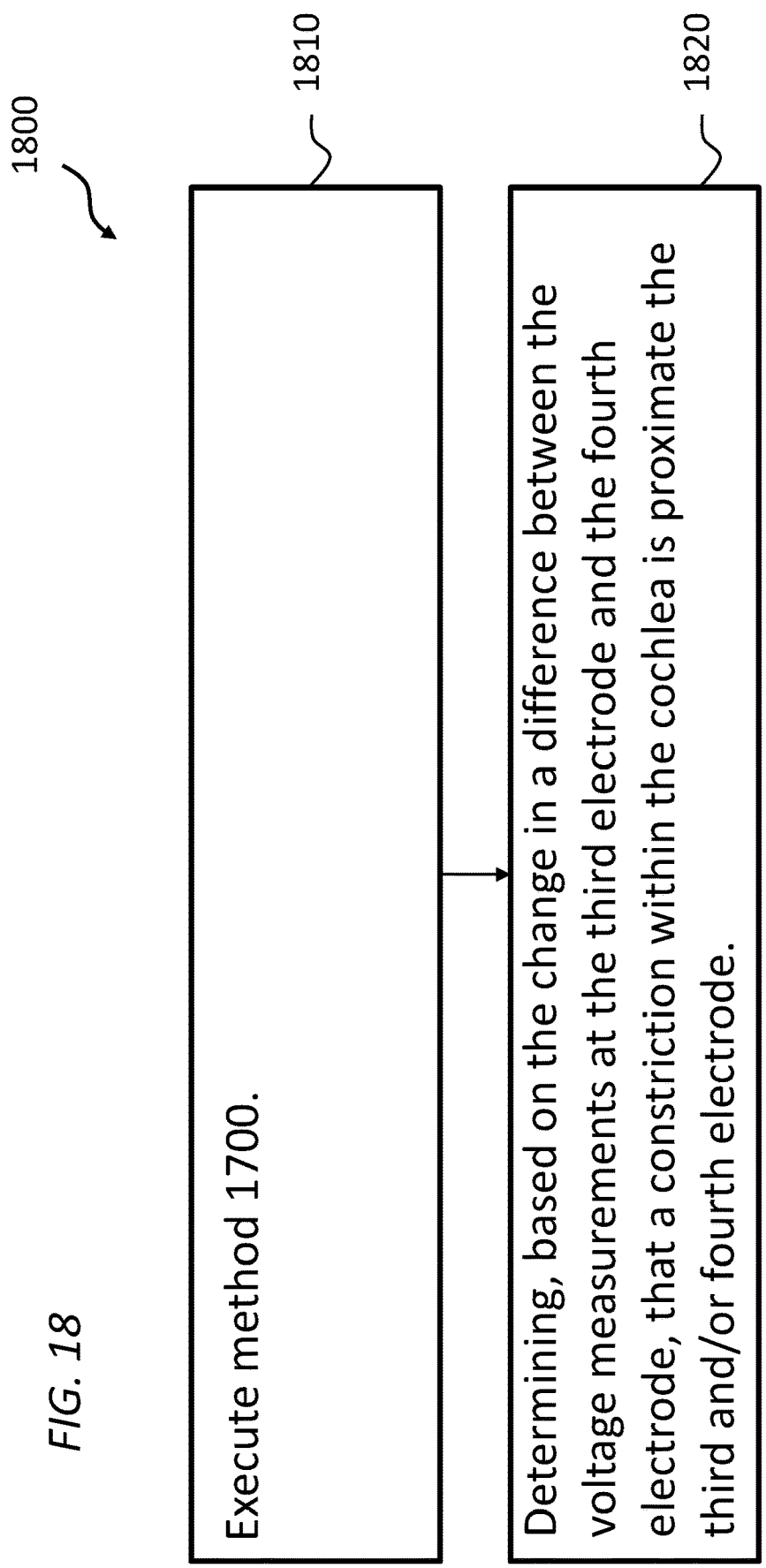

FIG. 18 presents another exemplary algorithm for an exemplary method, method 1800. Method 1800 includes method action 1810, which includes executing method 1700. Method 1800 also includes method action 1820, which includes determining, based on the change in a difference between the voltage measurements at the third electrode and the fourth electrode, that a constriction within the cochlea is proximate the third and/or fourth electrode. As can be seen, in an exemplary embodiment, the determination that the construction is proximate the third and/or fourth electrode can be made before the respective electrodes enter the construction. In an exemplary embodiment, a determination can be made that a constriction is within 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 11, 12, 13, 14, or 15 mm or any value or range of values therebetween in 0.05 mm increments of one or more of the third or fourth electrodes. In an exemplary embodiment, because the distance from the given electrodes to the most apical portion of the electrode array is known, a distance from the most apical portion of the electrode array to the constriction can be determined. The ability to determine such can have utilitarian value, as will be described in greater detail below.

In an exemplary embodiment, action of causing current to flow and measuring the voltage is executed during the first and second temporal locations while advancing the intra-cochlea electrode array into the cochlea of the recipient. By way of example only and not by way of limitation, a surgeon can be pushing the electrode array into the cochlea by hand (including utilizing an insertion apparatus). By way of example only and not by way of limitation, a robotic insertion device can be utilized to insert the electrode array into the cochlea. In an exemplary embodiment, the first and second temporal locations can correspond to discrete advancement distances of the electrode array. By way of example only and not by way of limitation, in an exemplary embodiment, measurements can be made, for example, at least every 5 mm, 4.5 mm, 4.0 mm, 3.5 mm, 3 mm, 2.5 mm, 2.0 mm, 1.5 mm, 1 mm, or 0.5, or 0.25, or 0.1 or 0.075 or 0.05 or 0.025 or 0.001 mm of electrode array advancement or any value or range of values therebetween in 0.001 mm increments. In an exemplary embodiment, a device that identifies the electrodes as they are moved forward can be utilized to determine the rate of advancement and to activate the measurements accordingly. In an exemplary embodiment, measurements can be made every 5, 4, 3, 2, 1, 0.75, 0.5, 0.25, 0.2, 0.1, 0.05, 0.04, 0.03, 0.02, 0.01 seconds, for example, or any value or range of values therebetween in 0.01 second increments, irrespective of the rate of advancement of the electrode array into the cochlea. In an exemplary embodiment, the number of measurements taken during a given temporal period can be correlated to the speed of the electrode array being inserted into the cochlea. For example, if the system of FIG. 5 identifies that the electrode array is being relatively rapidly inserted into the cochlea, the number of measurements for a given period of time will be higher than that which would be the case if the system determines that the electrode array is more slowly being advanced into the cochlea.

Also, owing to the fact that human beings sometimes have physiology that is the same as other human beings, an exemplary embodiment can take into account the fact that, all things being equal, statistically speaking, there typically is nothing of interest vis-á-vis the measurements until the first 5 or 6 or 7 or 8 or 9 or 10 or 11 or 12 or 13 or 14 or 15 or 16 or more electrodes are inserted into the cochlea. In this regard, no measurements are taken or otherwise the temporal spacing between the measurements and/or the distance of insertion between measurements is larger at the beginning of the insertion process than later in the insertion process.

Figure 22:
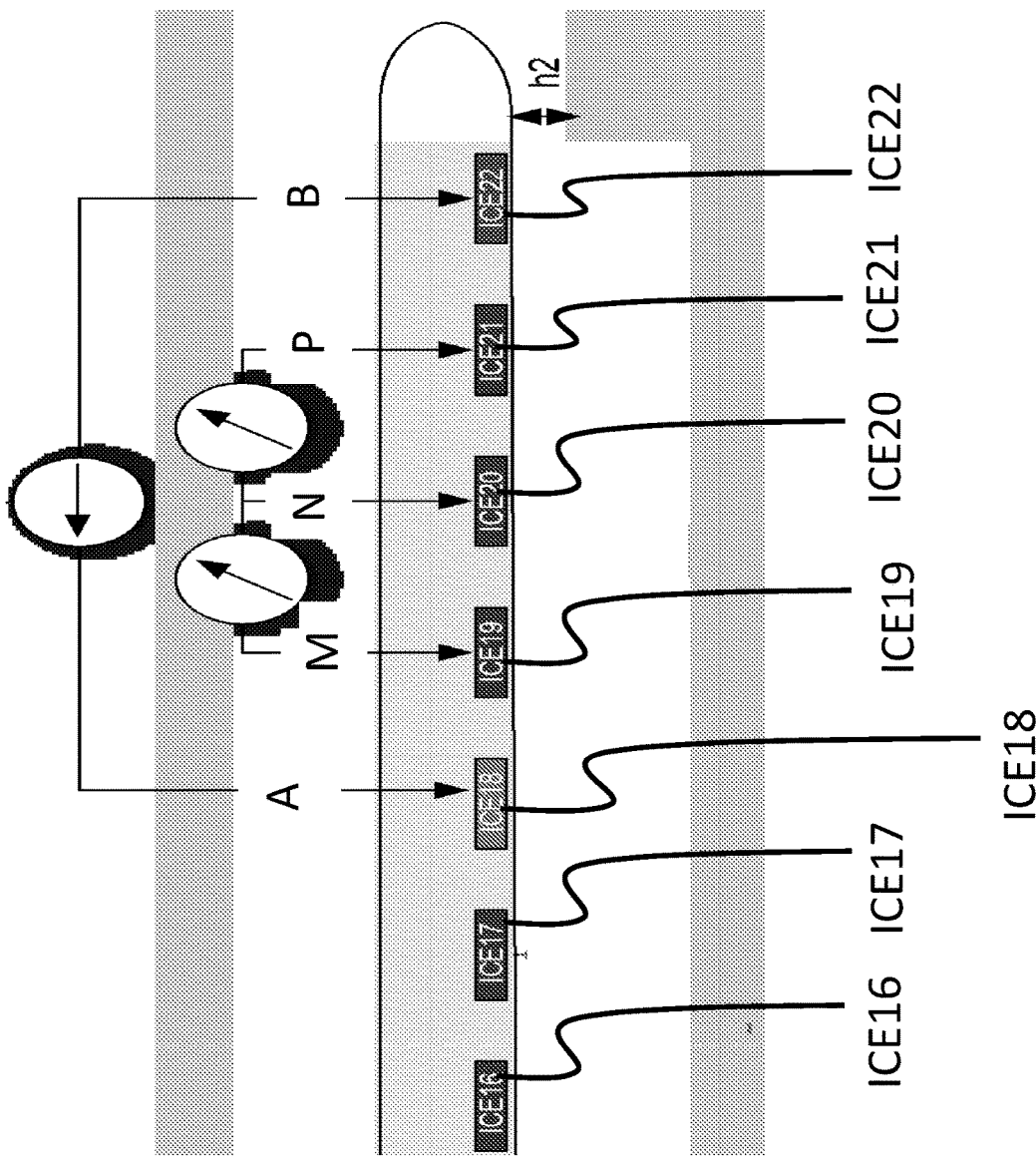

FIG. 22 conceptually presents a sudden constriction in a cochlea. That is, a constriction that occurs in a non-gradual manner, as compared to the tapered cylinder of FIG. 14. In some embodiments, this construction will affect the balance of the dipole before a stimulating electrode and/or a read electrode enters the narrowing. This is because, for example, the electrical field propagates in advance of the most apical electrode. This is utilitarian with respect to, for example, lateral wall electrode arrays, as sudden narrowing of the cochlear duct can be problematic these of the potential injury during electrode array insertion.

Figure 23:
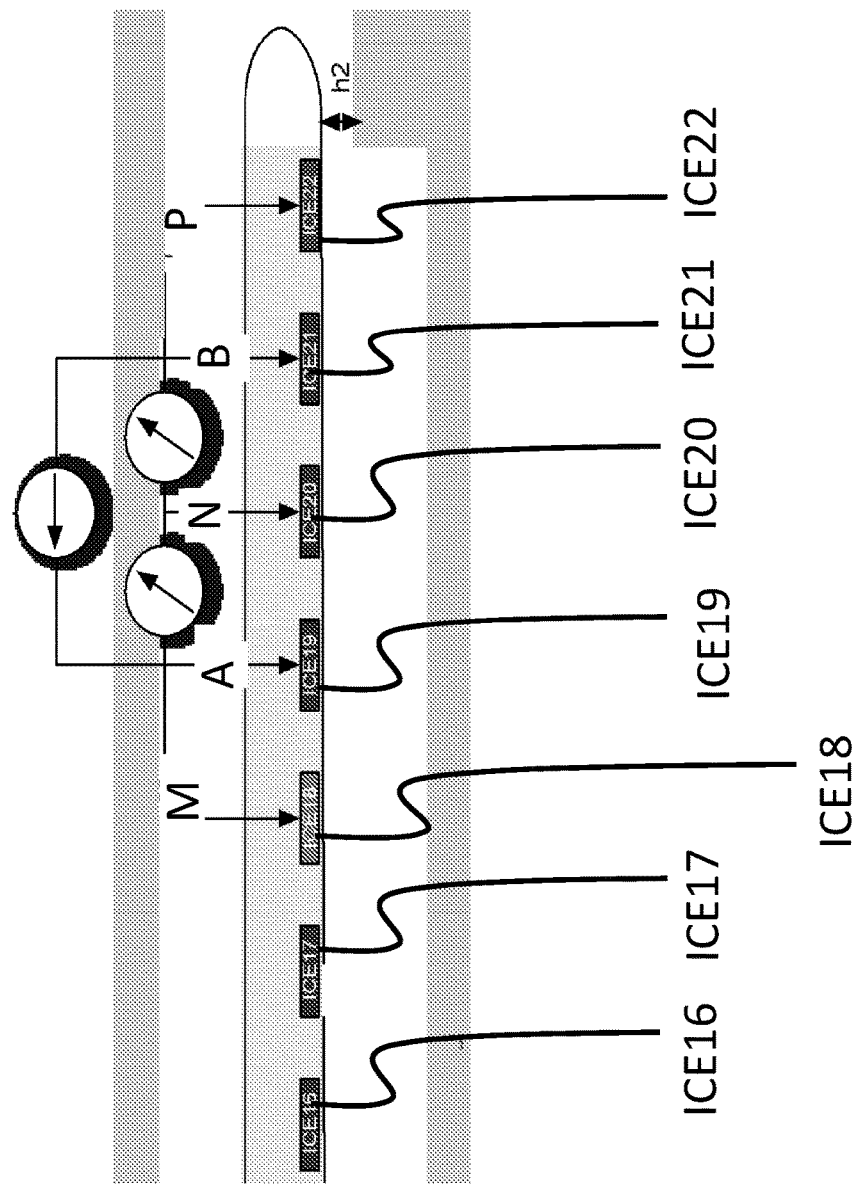

FIG. 23 depicts an alternative measurement paradigm for detecting dipole imbalance. It is not required to measure within the stimulating dipole, and FIG. 22 demonstrates such an alternate embodiment. It can be utilitarian to have the reference electrode equidistant from the stimulating electrodes, as it is utilitarian to detect a difference in the voltage gradient on either side of the theoretical null. Wider stimulation or recording setups are also possible, and can, in some embodiments, affect the sensitivity to different types of biological variations.

It is noted that constrictions need not persist to have an impact on the voltage gradient. In this regard, even a temporary constriction, shown in FIG. 11, will increase the electrical field gradient around the constriction, which can make such noticeable. Thus, it can be seen that these measurements corresponding to the results detailed above are biomarkers, in that they can be characteristic features of the measured signal which are induced by systematic biological variations in the cochlear.

In an exemplary embodiment of methods 1700 and 1800, the action of causing current to flow and measuring the voltage is executed during the first and second temporal locations while advancing the intra-cochlea electrode array into the cochlea of the recipient. That is, in this exemplary embodiment, the electrode array is moving inward while the current is flowing. It is noted that this is a species of the genus of electrode array insertion. That is, the actions of causing current to flow and measuring the voltage is can be executed during an electrode array insertion process, but that does not mean that the electrode array must be moving while the voltages are measured and the currents are generated. Thus, in an alternate embodiment, the electrode array is stationary while the action of causing current to flow and measuring the voltage is executed. In some instances, sometimes, the electrode array is being moved forward and in other instances the electrode array is stationary.

In accordance with the teachings detailed above, in an exemplary embodiment, methods 1700 and/or 1800 also include the action of, based on the determination that a change in a difference between the voltage measurements has occurred, halting advancement of the electrode array into the cochlea. It is noted that this additional action can be executed in a manner that entails the halting of pushing the electrode array forward, while in other exemplary embodiments, this can entail stopping further insertion where, upon the determination that no further insertion should occur, the electrode array was stationary. With regards to the slider embodiment, an exemplary insertion method can correspond to inserting the electrode array a certain amount, and then stopping, and then taking the measurements and making the determinations prior to inserting the electrode array further into the cochlea. This as opposed to the embodiment where the measurements are being taken and the determination is made while the electrode array is being moved further and further into the cochlea, and then stopping.

In an exemplary embodiment, the voltage at the third electrode and the voltage at the fourth electrode is measured relative to a fifth electrode of the intracochlear electrode array located in the cochlea. Consistent with some of the embodiments above, in an exemplary embodiment, the third and the fourth electrodes are disposed symmetrically about the fifth electrode (the reference electrode). That said, in some alternative embodiments, the third and the fourth electrodes are not disposed symmetrically about the fifth electrode. Any arrangement of electrodes that can be utilized to practice the teachings detailed herein can be utilized in at least some exemplary embodiments.

Also consistent with the teachings detailed above, the third and the fourth electrodes can be disposed between the first and the second electrodes, while in some other embodiments, the first and the second electrodes are disposed between the third and the fourth electrodes. In an exemplary embodiment, both of the stimulating electrodes and the two read electrodes (which is utilized for shorthand—in reality, the reference electrode is also a read electrode) are arrayed symmetrically about the reference electrode, while in other embodiments, only the two read electrodes but not the two stimulating electrodes or vice versa are arrayed symmetrically about the reference electrode. Still further, in some embodiments, neither the two stimulating electrodes nor the two read electrodes are arrayed symmetrically about the reference electrode. Of course, in a scenario where, for example, more than two read electrodes are utilized, such as where all of the electrodes other than the stimulating electrodes are utilized as read electrodes, there will be scenarios where some read electrodes are arrayed about the reference electrode in a symmetrical manner and others are not.

Owing to the utility of utilizing the teachings detailed herein to enable the electrode array to function as a probe or the like, it is to be understood that in at least some exemplary embodiments, the first electrode detailed above is disposed at an apical and of the intra-cochlea electrode array, and/or the second electrode is disposed basally of the third and fourth electrodes. In this regard, for a 22 electrode array, the first electrode would be electrode 22 (where electrode 1 is the most basal electrode). For a nine electrode array, the first electrode would be electrode nine, and so on.

In an exemplary embodiment, the action of causing current to flow and measuring the voltage in method 1700 and/or 1800 is executed during the first and second temporal periods while advancing the intra-cochlea electrode array into the cochlea of the recipient, and the first temporal period and the second temporal period establish an overall temporal period lasting the time that it took to insert the electrode no more than Z mm into the cochlea, where Z equals 0.001, 0.0025, 0.05, 0.075, 0.1, 0.15, 0.2, 0.25, 0.3, 0.35, 0.4, 0.45, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 11, 12, 13, 14, or 15 or any value or range of values therebetween in 0.01 mm increments.

Figure 19:
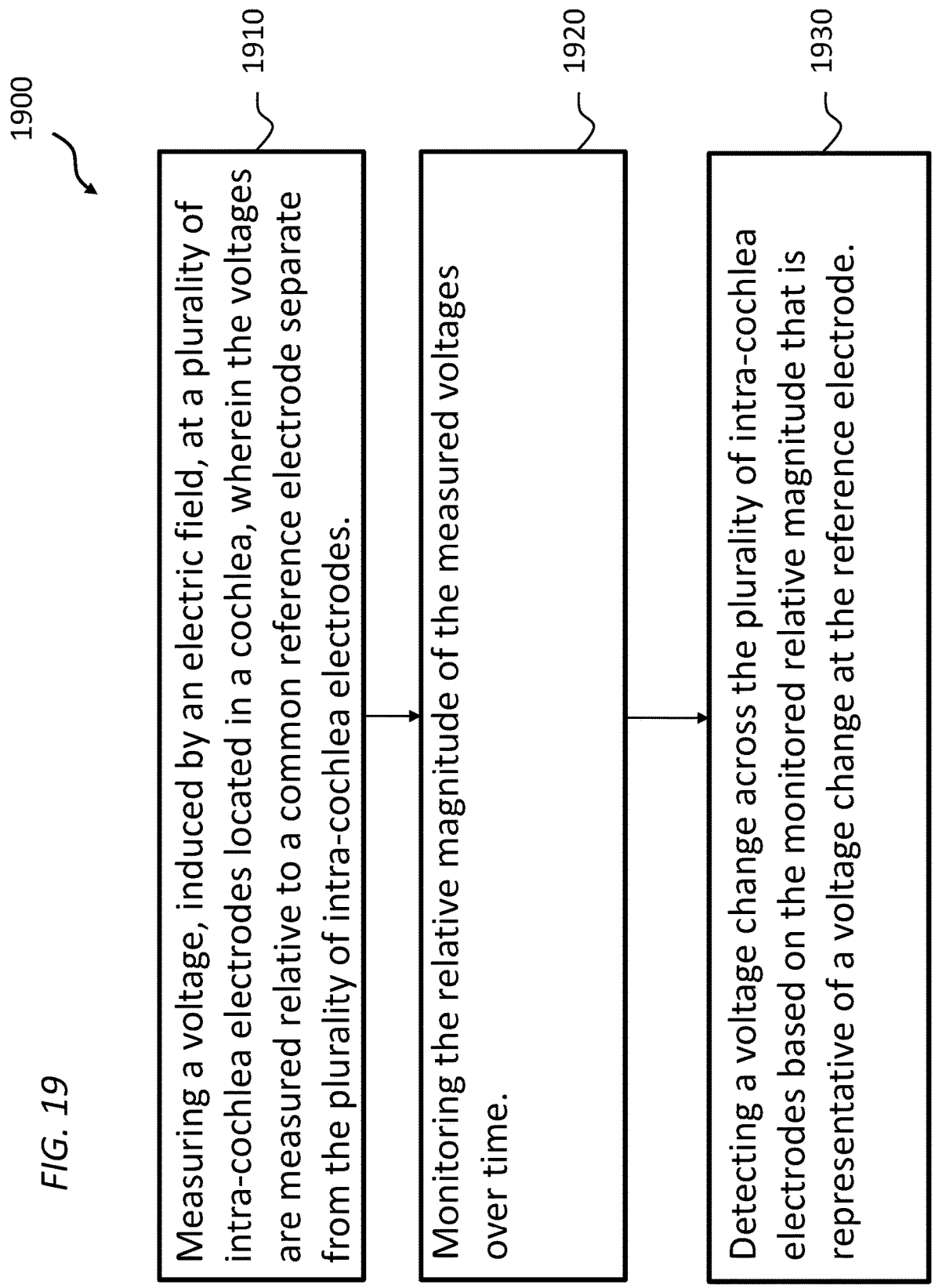

FIG. 19 presents an alternative algorithm for an alternative method, method 1900. Method 1900 includes method action 1910, which includes measuring a voltage, induced by an electric field, at a plurality of intra-cochlea electrodes located in a cochlea. In method action 1910, the voltages are measured relative to a common reference electrode separate from the plurality of intra-cochlea electrodes where the measurements are taken. This is not to say that the common reference electrode is not an electrode of the electrode array. Just the opposite. As seen above, the reference electrode is an electrode that can be part of the electrode array located between the read electrodes. Still, in some embodiments, it is possible that the common reference electrode can be an electrode located outside the cochlea.

Method 1900 also includes method action 1920, which includes monitoring the relative magnitude of the measured voltages over time. In this regard, the actual voltages can be measured, while in other embodiments, simply a change in the voltages can be monitored. Any method that would entail monitoring relative magnitude of the measured voltages over time can be utilized in at least some exemplary embodiments. In view of the insertion methods detailed above, in an exemplary embodiment, the "overtime" corresponds to a time in which the electrode array was further inserted into the cochlea relative to that which was the case the beginning of the time.

Method 1900 also includes method 1930, which includes detecting a voltage change across the plurality of intra-cochlea electrodes based on the monitored relative magnitude that is representative of a voltage change at the reference electrode. In some embodiments of method 1900, the electric field comprises an electric dipole formed by stimulating between two intra-cochlea electrodes in the cochlea, and in some further embodiments, the reference electrode is disposed between the two stimulating intra-cochlea electrodes. In some embodiments, method 1900 includes the action of sourcing currents at a first intra-cochlea electrode, and sinking current at a second intra-cochlea electrode, to create the electric field. It is noted that in some exemplary embodiments, the electric field is a control electric field that is controlled via, for example, the receiver stimulator and where the system is in signal communication therewith to establish a predetermined field of a predetermined strength so that the data that is obtained by measuring the voltages can be compared against other data so as to determine whether or not a phenomenon exists based on the comparison.

In an exemplary embodiment, the voltage change from a first temporal location to a second temporal location is due to compression of an electrical field around an apical portion of a cochlea electrode array of which the plurality of intra-cochlea electrodes are apart. In an exemplary embodiment, the compression amounts to at least 1, 2, 3, 4, 5, 6, 7, 8, 9, 10, 15, 20, 25, 30, 35, 40, 45, 50, 55, 60, 65, 70, 75 or 80% or more relative to that which was the case at a previous temporal location.

Figure 20:
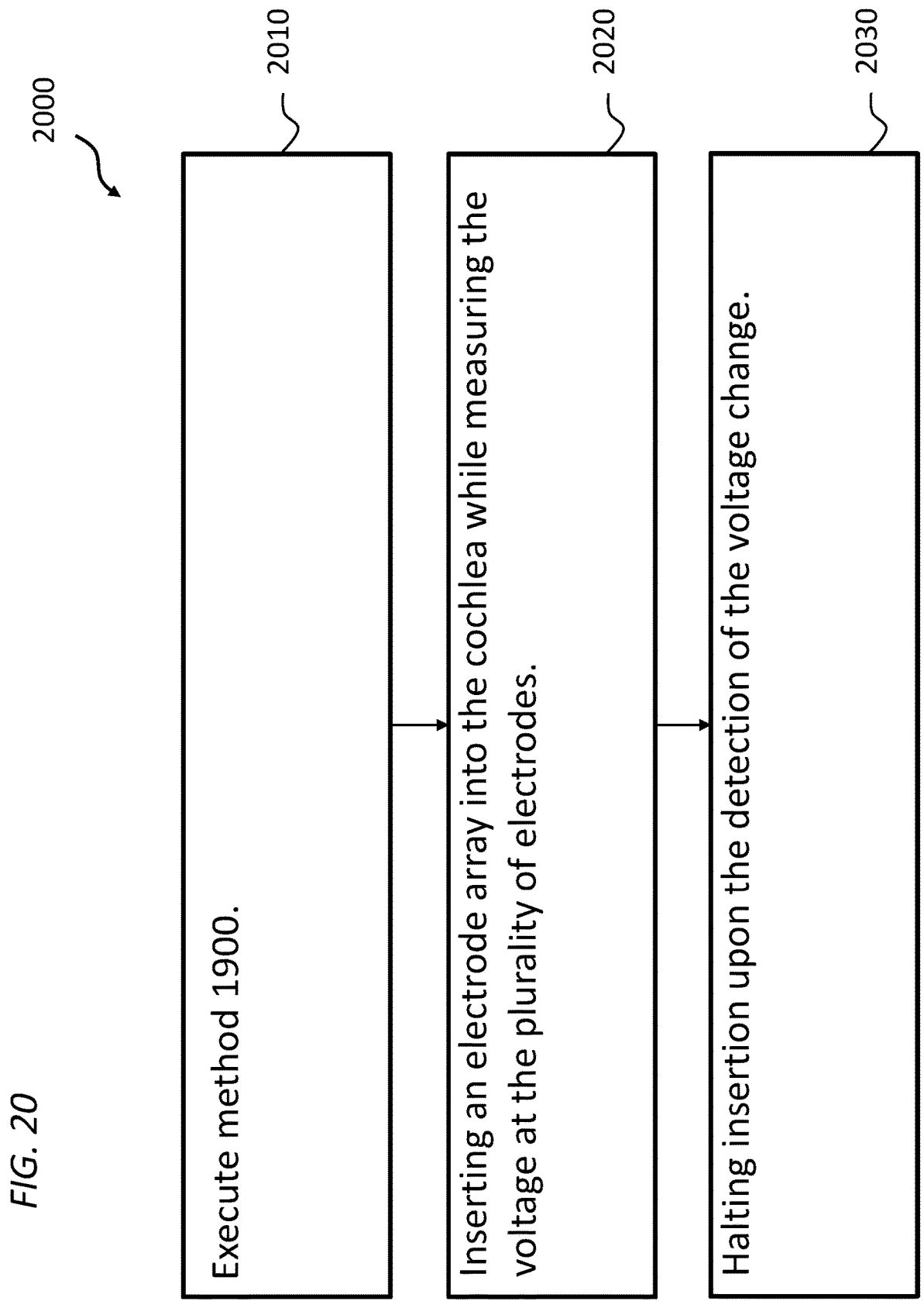

In an exemplary embodiment, the change in voltage occurs simultaneously at respective electrodes of the plurality of intra-cochlea electrodes. In an exemplary embodiment, the change in voltage can correspond to something along the lines of that which is represented in FIG. 16. In an exemplary embodiment, the plurality of electrodes includes at least J electrodes, and the change in voltage occurs simultaneously at the respective electrodes of the plurality of intra-cochlea electrodes. In an exemplary embodiment, J equals 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more or any range of values therebetween in integer increments. In some embodiments, the voltage change at the reference electrode impacts all voltage measurements at the plurality of electrodes equally. Thus, in some instances, the plurality of electrodes includes at least J electrodes, and the voltage change at the reference electrode impacts all voltage measurements at the plurality of electrodes equally. Also, in some instance, again where there are J electrodes (at least), the voltage change at the reference electrode impacts all voltage measurements at the plurality of electrodes equally, which change occurs simultaneously at the 10 respective electrodes of the plurality of intra-cochlea electrodes. In this regard, the concept of FIG. 16 is that not just one electrode shifts (the readings therefrom, that is), but the measurements on all electrodes reference the same point shift in the same direction by a similar magnitude. The changes in the voltage due to a shift in the reference should impact all electrodes equally, at least in some embodiments. In some instances, there are two or three factors at play in the curve in FIG. 16: (1) a shift in the reference null point, and/or (2) current is migrating between the cochlear turns, through the modiolus or lateral wall, suppressing the voltage at the basil end of the array—in some instances, this occurs because the apical electrode (E22) has the opposite polarity to the basil stimulating electrode (E18). FIG. 20 depicts another exemplary algorithm for an exemplary method, method 2000. Method 2000 includes method action 2010, which includes executing method 1900 as detailed above. Method 2000 also includes method action 2020, which includes the action of inserting an electrode array into the cochlea while measuring the voltage at the plurality of electrodes. Thus, it is to be understood that method action 2020 can be executed while some of the method actions and/or all of the method actions of method 1900 are executed. It is also noted that in at least some exemplary embodiments, while the algorithms are presented in an order as seen, in some instances, the order is different than that presented. In this regard, any of the methods detailed herein can be executed such that any given method action can be executed in any order relative to any other method action, providing that the art enables such or otherwise specifically stated.

Method 2000 also includes method action 2030, which includes the action of halting insertion upon the detection of the voltage change. It is noted that the action of halting insertion can include both stopping insertion where previously, the electrode was being pushed into the cochlea, and the action of not further inserting the electrode array into the cochlea where upon the determination that the action of halting to be executed, the electrode array was stationary.

Figure 21:
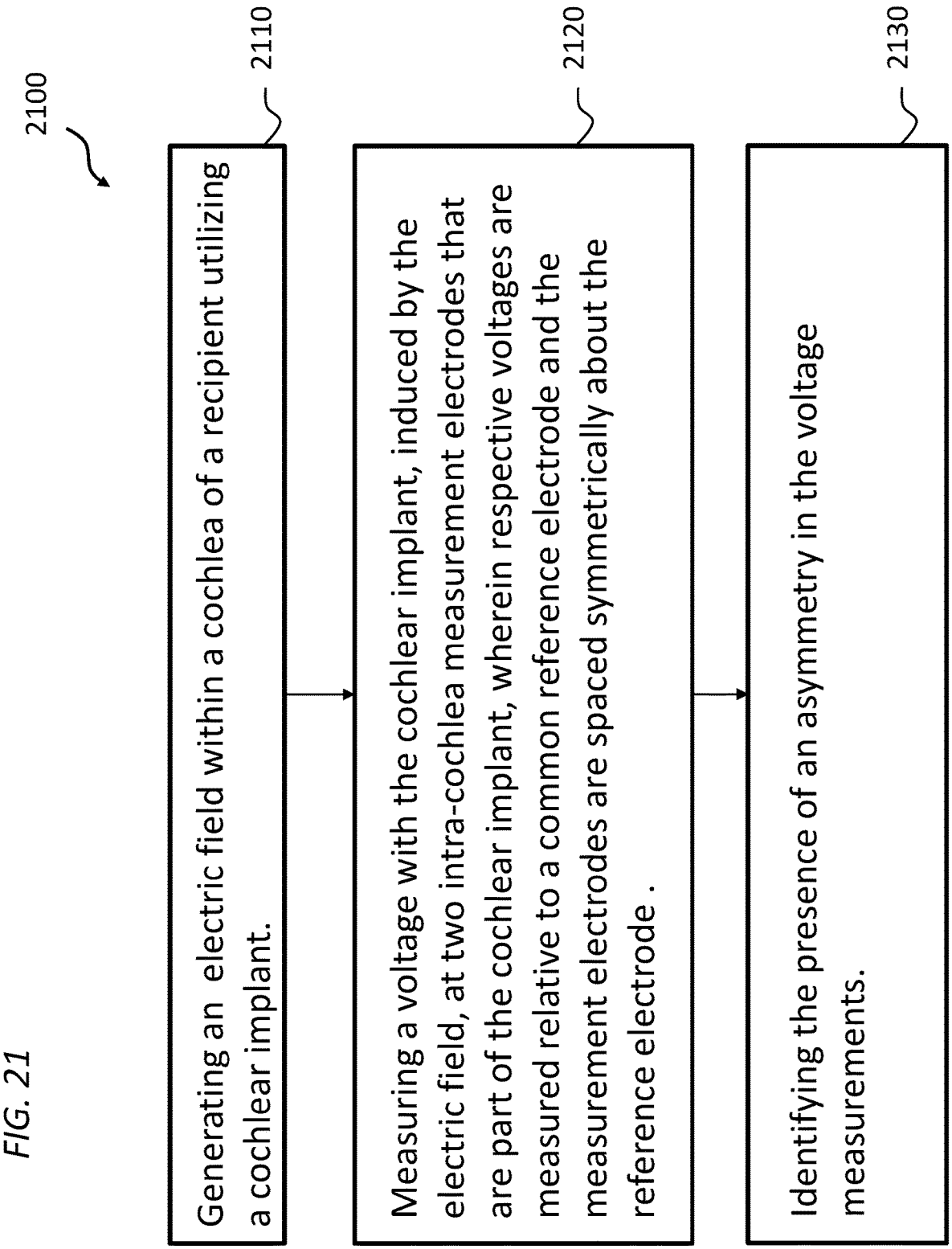

FIG. 21 presents another exemplary algorithm for another exemplary method, method 2100. Method 2100 includes method action 2110, which includes generating an electric field within a cochlea of a recipient utilizing a cochlear implant. This can be done by applying alternating current to two electrodes of the electrode array in accordance with the teachings detailed above. Method 2100 also includes method action 2120, which includes measuring a voltage with the cochlear implant, induced by the electric field, at two intra-cochlea measurement electrodes that are part of the cochlear implant. In an exemplary embodiment, respective voltages are measured relative to a common reference electrode and the measurement electrodes are spaced symmetrically about the reference electrode. Method 2100 also includes method action 2130, which includes identifying the presence of an asymmetry in the voltage measurements. In some embodiments, the identified asymmetry in the voltage measurements is due to a constriction within the cochlea and/or due to a narrowing of the cochlea. In an exemplary embodiment where the narrowing is the basis for the asymmetry, in some exemplary embodiments, the narrowing is a pronounced narrowing relative to any other prior narrowing within the cochlea relative to distance within the cochlea from the basil and to the apical and that causes the asymmetry to be pronounced relative to any asymmetry that previously existed or otherwise was identified.

In this regard, it is noted that the action of identifying the presence of an asymmetry in the voltage measurements includes identifying the presence of a significant asymmetry in the voltage measurements. In this regard, asymmetry can exist in some instances for various reasons, such as, for example, a nonsignificant narrowing of the cochlea, and/or a cochlear electrode array that is extending at an angle relative to the local longitudinal axis of the cochlea relative to the read electrodes and/or the stimulating electrodes, such that one or more of these electrodes is closer to the wall than the other, etc. In some exemplary embodiments, the presence of the asymmetry is thus a significant asymmetry. In an exemplary embodiment, in an alternate method or variation of method 2100, method action 2130 includes, in addition to this or instead, the action of identifying that the asymmetry in the voltage measurements has changed. In an exemplary embodiment, this can include determining that a significant change has occurred. In an exemplary embodiment, the change in the asymmetry can correspond to at least more than a 10, 20, 30, 40, 50, 60, 70, 80, 90 100, 125, 150, 175, 200, 225, 250, 275, 300, 350, 400, 450, 500, 550, 600, 650, 700, 800, 900, 1000, 1250, 1500 percent change or more or any value or variations of values therebetween in 1% increments relative to that which existed at a prior temporal period. In an exemplary embodiment, the aforementioned change can occur within any of Z mm of insertion.

Accordingly, in view of the above, it is to be understood that in an exemplary embodiment, when practicing method 2100, the method can further include detecting asymmetry in the voltage prior to detecting the asymmetry and/or detecting asymmetry in the voltage that is different from the asymmetry detected in method 2100. To be clear, some embodiments detailed herein are such that any disclosure herein of a previously detected asymmetry that was deemed not significant also corresponds to a disclosure of a symmetric field.

In view of the above, in an exemplary embodiment, method 2100 can be practiced by first identifying any number of symmetric electrical fields and/or any number of insignificantly asymmetric electric fields and then identifying the presence of a significantly asymmetric electric field, and based on the latter identification, determining that one should halt insertion of the electrode array or otherwise determine that the electrode array should not be advanced any further, at least not without taking additional action.

An exemplary method also includes executing method 2100, while further executing the action of determining a location of an apical end of an electrode array within the cochlea based on the detected asymmetry, wherein the electrode array is part of the cochlear implant and includes the two intra-cochlea measurement electrodes. In an exemplary embodiment, because the locations of the read electrodes are known relative to the overall structure of the cochlear electrode array, the distance to the apical and of the electrode array can be known beforehand. Thus, based on the identified asymmetry, the apical end of the electrode array within the cochlea can be estimated. This is because, in at least some exemplary embodiments, the phenomenon that causes the asymmetry within the cochlea causes such in a predictable manner amongst a statistically significant population of people who have cochleas. In an exemplary embodiment, this can correspond to a biomarker. Thus, because a correlation can be developed between the resulting measurements electrodes and the statistically significant population, and because the resulting measurements are reproducible across the statistically significant population and occur in about the same location within the cochlea for the statistically significant population, by knowing the geometry of the electrode array, the location of the apical end of the electrode array in the cochlea can be determined.

Figure 24:
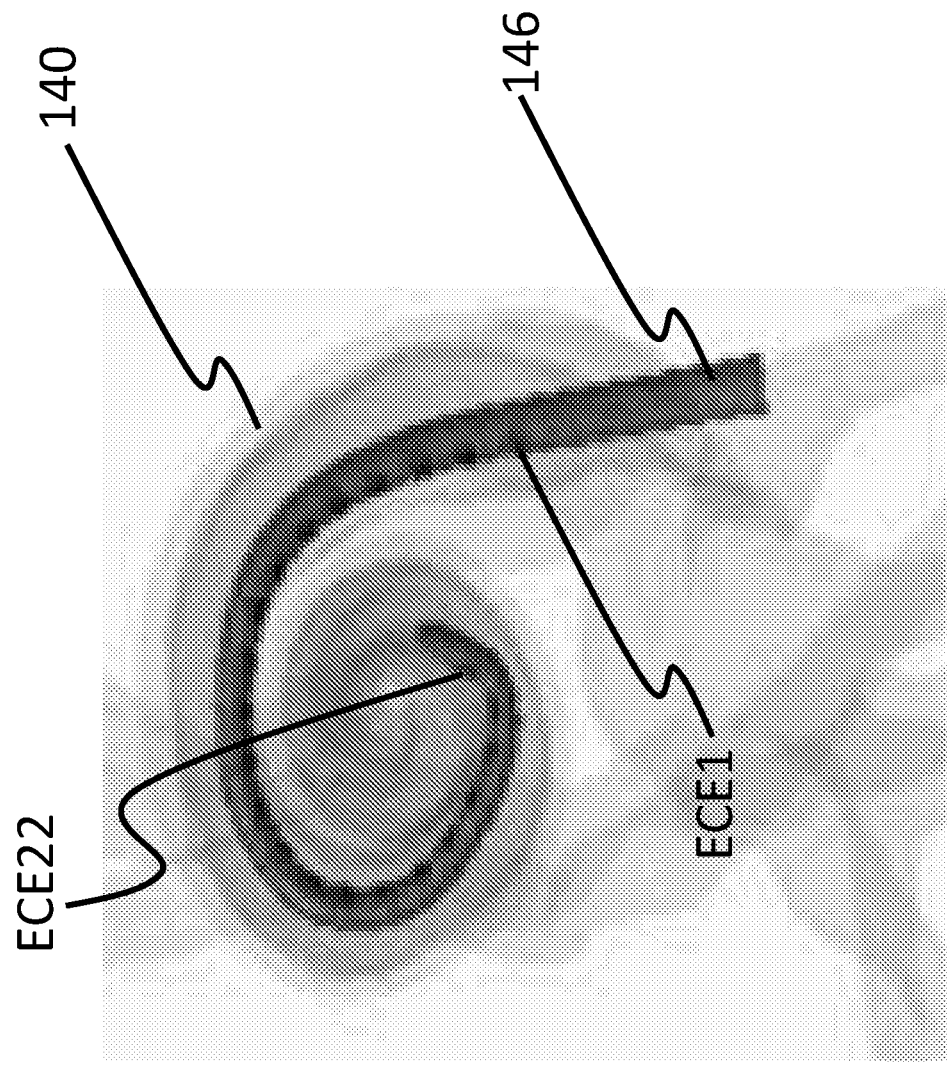
FIGS. 24-31 provide schematics of some exemplary electrode insertion regimes.

In this regard, FIG. 24 depicts an exemplary location of a cochlear electrode array 146 within a cochlea 140 where the geometry of the cochlea in the area proximate the apical end of the electrode array is such that the aforementioned asymmetry phenomenon exists when the read electrodes are positioned as shown and/or where the makeup of the electrode array 146 is such that, in a typical cochlea of a statistically significant population, because the electrode arrays for the respective insertions are generally the same, the aforementioned asymmetry phenomena exist.

In an exemplary embodiment, the shift depicted in FIG. 16 that can be inferred by measuring the DC offset of an entire measurement signal (using all the available electrodes) occurs when the electrode array is positioned as shown in FIG. 24. In at least some exemplary embodiments, this is because a change at the reference electrode will impact all measurements based on the reference simultaneously and/or equally. This technique is used to identify a biomarker in the cochlea/associated with the cochlea, which indicates, for example, the selected the insertion positions of the electrode array schematically represented in FIG. 24.

Figure 25:
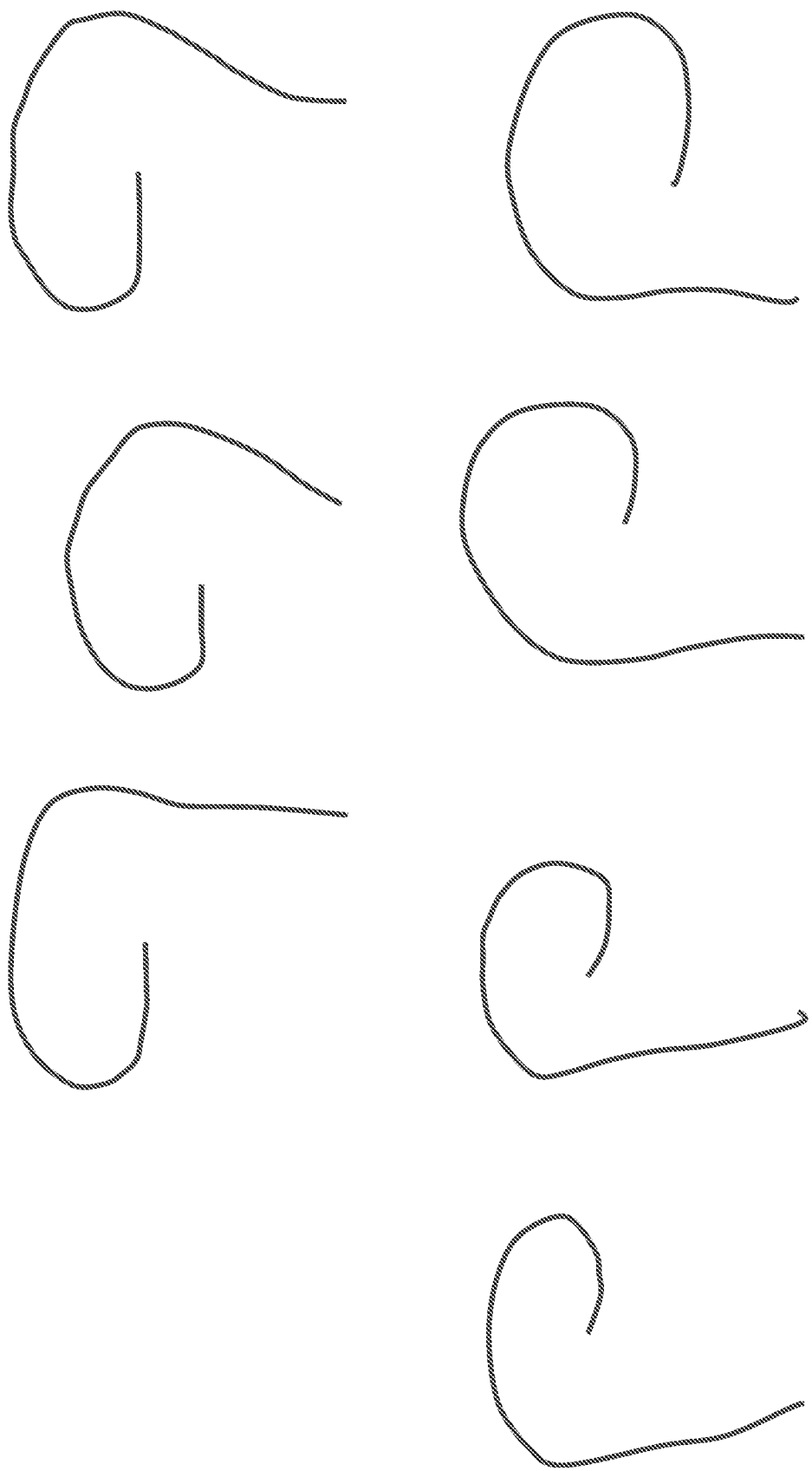
Figure 26:
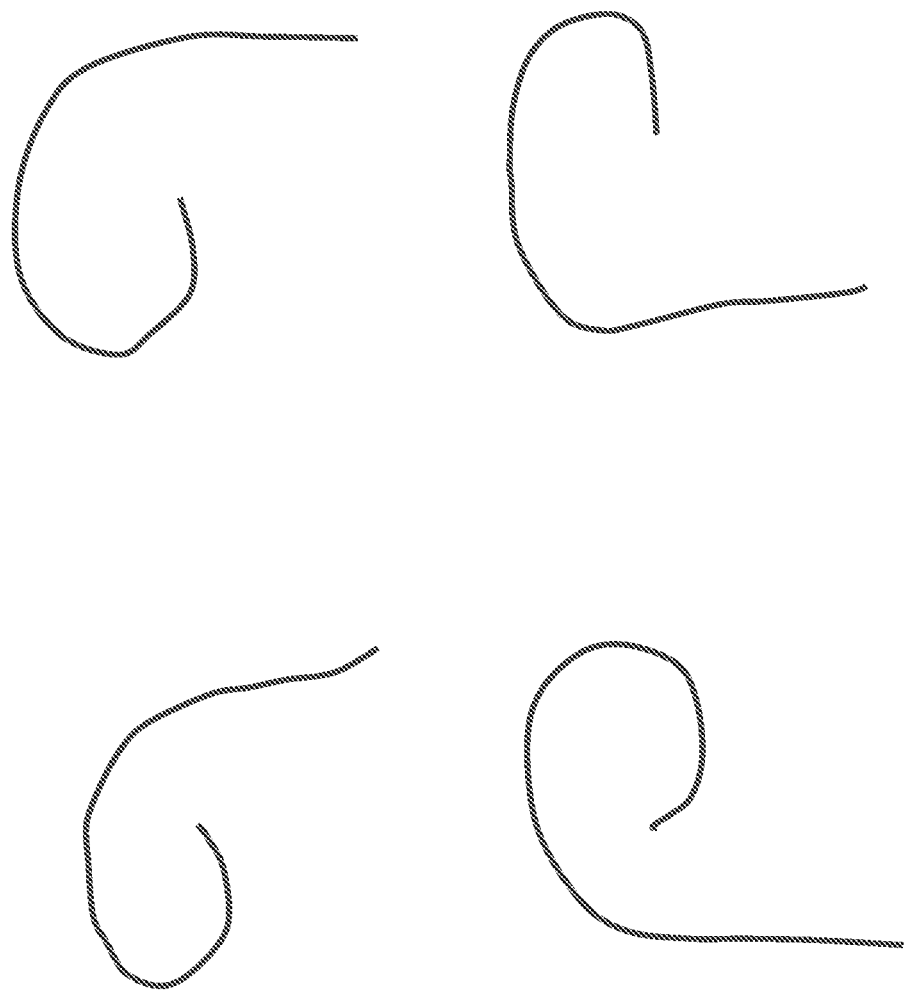
Figure 27:

FIGS. 25 and 26 depict conceptual geometries of the electrode array where electrodes are arranged as shown in FIG. 23, resulting in the voltage phenomena detailed herein at the read electrodes (note that these are for a perimodiolar insertion, as opposed to a lateral wall, where the radius of curvature would be larger and thus the angular curvature would be less). As can be seen, the general geometry of the electrode array is the same over those examples. In an exemplary embodiment, these figures are to scale, where the most apical electrode array is located at the tip of the curled line. FIG. 27 presents an exemplary geometry of an electrode array with electrodes imposed thereon (the circles), in a scaled manner, which can correspond to the placement of the electrodes in FIGS. 25 and 26 (again for perimodiolar insertion). In an exemplary embodiment, the biomarkers detailed herein (asymmetry of the electric field, the compression of the electric field, the change in baseline voltage, etc.) occur or otherwise are encountered or otherwise measured when the electrode array takes one of the shapes depicted in FIGS. 23-26/the electrodes of the electrode array are arrayed according to one of the shapes shown in FIGS. 23 to 26/the apical tip will be located in accordance with the teachings associated with FIGS. 28-31. As will be detailed further below, the biomarkers can thus be utilized to at least estimate or otherwise determine the location of the distal end of the electrode array and/or the entire array for that matter, and thus evaluate whether additional insertion of the electrode array can be utilitarian or otherwise to determine that no additional insertion is needed. In an exemplary embodiment, the teachings detailed herein are utilized so as to affect an electrode array placement according to those detailed in FIGS. 23 to 26 (where centers of the electrodes generally (at least) follow the curves shown) and/or in accordance with the data associated with FIGS. 28-31. In an exemplary embodiment, the schematics of FIGS. 23-26 correspond to that which results from an X-ray or other imaging 2 dimensional product.

In an exemplary embodiment, the electrode arrays having the locations according to FIGS. 23 to 26 correspond to a so-called 270° turn electrode array insertion. That is, the apical end of the electrode array and/or the most apical electrode is located at the 270° turn within the cochlea. It is noted that in at least some exemplary embodiments, this can result in one or more electrodes of the electrode array not being located in the cochlea.

An alternate exemplary embodiment includes executing method 2100 along with additional actions, such as the action of pushing an electrode array into a cochlea, wherein the electrode array is part of the cochlear implant and includes the two intra-cochlea measurement electrodes. This method further includes the action of detecting at least one of a symmetry or a partial asymmetry (an insignificant asymmetry will be defined by the phrase partial asymmetry) during a first temporal period during pushing of the electrode array into to the cochlea, and continuing to push the electrode array after detecting such. The method further includes the action of halting the pushing of the electrode array into the cochlea upon detecting the asymmetry, wherein the detection of the asymmetry occurs during a second temporal period after the first temporal period. In this regard, the asymmetry is a full asymmetry or otherwise a significant asymmetry, as opposed to the previous partial asymmetry. Note also that in a variation of the aforementioned method, the detection of at least one of the symmetry were a partial asymmetry need not be executed while pushing the electrode array. In an exemplary embodiment, such can be detected in an intervening period where the electrode array is no longer being pushed forward. Again, in an exemplary embodiment, the method of inserting the electrode array can entail a regime corresponding to push forward, stop, read, evaluate, push forward, stop, read, evaluate, push forward, stop, read, evaluate push forward, stop, read, evaluate, do not push any further forward. Alternatively, the method of inserting the electrode array can entail a regime corresponding to pushing forward and reading and evaluating while pushing forward and repeating the reading and evaluating while pushing forward until an evaluation indicates that the pushing should stop. Note that the two types of regimes can be intermingled with one another.

It is briefly noted that in some embodiments, there will always be a modicum of asymmetry in a cochlea, but sensitivity is limited both by the sampling capabilities of the implant, and also the quantum of variation which can be sensed at the electrode surface. Also, electrode pads are different sizes, and with respect to modiolar proximity, once you get beyond about 3× the separation of the stimulating electrodes the data becomes unwieldly with respect to the impact on the measurements. Thus, the measurements are, in some embodiments, based on thresholds or averages and otherwise take into account that there will always be a "nose" level that is addressed. That is, in some embodiments, the asymmetries detailed herein are "significant" in that they are beyond that which results from the limitations of the technology in obtaining perfect measurements and/or beyond that which results from the fact that the cochlea is not a perfect cylinder.

Moreover, at least some of the embodiments that deal with asymmetry cover the scenario where there is an initial asymmetry which becomes a symmetry. For example, there can be a scenario where one can have the apical electrode coming out of the sheath and touching the modulus before the second sense electrode emerges. One will start in a case of asymmetry, however if the second sense electrode also comes into contact with the modiolus, one will will get a substantial baseline shift as the system returns to "symmetry." This behavior may be related to electrode dynamics such that it occurs in approximately the same depth for a given electrode type, providing a marker of sorts.

Figure 28:
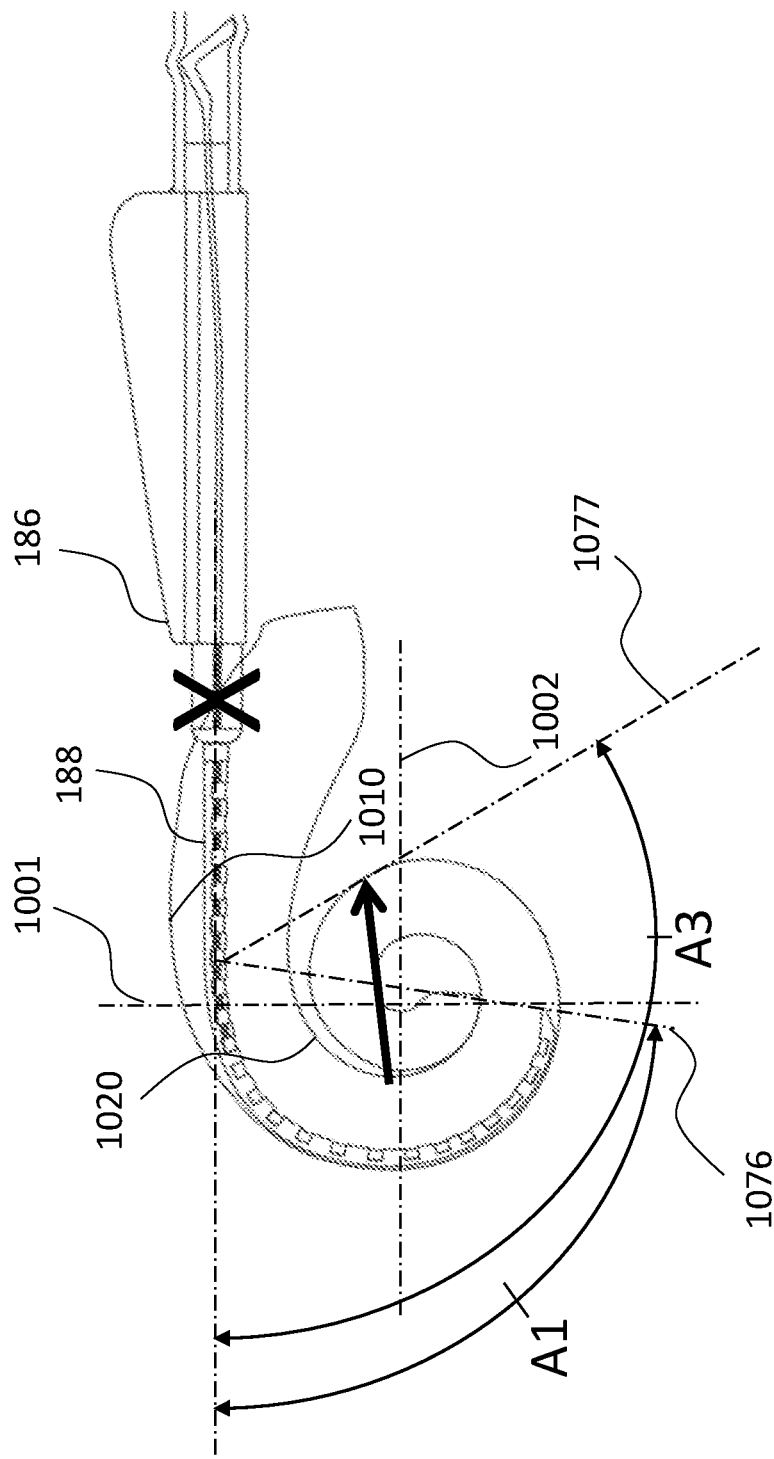
Figure 29:
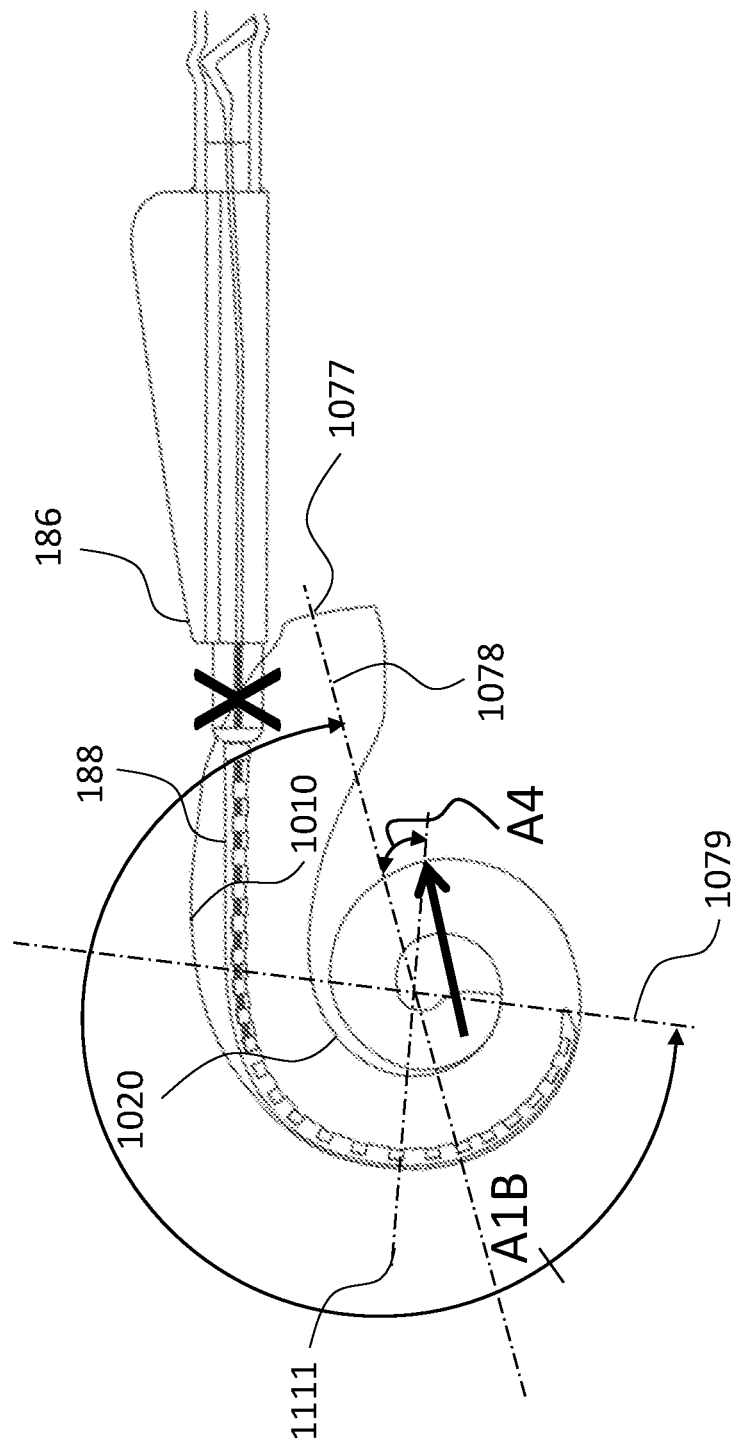

FIGS. 28 and 29 depict, for conceptual purposes only, an exemplary angular depth, where the first distance is measured from the tip of the electrode array to the X through the longitudinal axis of the intra-cochlea electrode portion 188 of the electrode array. More specifically, FIGS. 28 and 29 depict a cross-sectional compressed view of a human cochlea with a lateral wall 1010 and a modiolus wall 1020 with an electrode array therein at a first geometry (again, for conceptual purposes only). In FIG. 28, the orientation of the electrode array, relative to the location where the electrode array begins to curve (line 1076 extends through the point where the array begins to curve to the tip of the array), is 90 degrees plus A1, which, based on the scale of FIG. 28, is about 170 degrees. With respect to the axis 1001 and 1002, which is static in that it is based on the geometry of the cochlea (centered on the modiolus, with the axis 1002 parallel to the direction of insertion of the electrode array at the point the electrode array enters the cochlea in the first geometry), the electrode array subtends an angle of 180 degrees. That is, the angular depth is such that the electrode array in general, and the intra-cochlear portion in particular, subtends an angle of about 180 degrees.

In an exemplary embodiment where the tip of the electrode array is inserted further into the cochlea than that depicted in FIG. 28, where, for example, the tip of the electrode is located at about the location identified by the tip of the large arrow, the angle A3 (measured off of line 1077, which passes through the point where the array begins to curve and the tip of the arrow) would be about 120 degrees where the above asymmetry features would first be seen (e.g. the phenomenon of FIG. 16 would occur when the tip reached that angle). In an exemplary embodiment, A3 is about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160 degrees, or any value or range of values therebetween in 0.1 degree increments. Note that this is for a relatively long array in the lateral wall hugging configuration. In other embodiments, the "arrow" would be at about the 6 O'clock position at the bottom of the cochlea (about where the tip is shown in FIG. 28) for a lateral wall hugging array. Thus, angle A3 could equal A1.

With respect to FIG. 29 (and FIG. 31), this figure depicts a frame of reference depicting the first insertion depth as measured from the axis 1078 that passes through the round window 1077 (e.g., depicting a traditional frame of reference for angular insertion depth, using the round window to establish one of the axes, as differentiated from the arrangement of FIG. 28), where axis 1078 and axis 1079 extend through the traditional center used to calculate insertion depth. The initial insertion depth is about 250 degrees. With respect to the axis 1078 and 1079, which is static in that it is based on the geometry of the cochlea (centered on the modiolus, with the axis 1078 passing through the round window 1077) the electrode array subtends an angle of A1B1. That is, the angular insertion depth is such that the electrode array in general, and the intra-cochlear portion in particular, subtends an angle of about 250 degrees when fully inserted into the cochlea.

In an exemplary embodiment where the tip of the electrode array is inserted further into the cochlea than that depicted in FIG. 29, where, for example, the tip of the electrode is located at about the location identified by the tip of the large arrow (in some embodiments, the arrow is further down), the angle as measured from axis 1078 to axis 1111 would be about 350 degrees (around once and then 15 degrees more), where the above asymmetry features would first be seen (e.g. the phenomenon of FIG. 16 would occur when the tip reached that angle). In an exemplary embodiment, A1B is about 90 degrees plus 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190 degrees, or any value or range of values therebetween in 0.1 degree increments. A4 could be about −15, 14, 13, 12, 11, 10, 9, 8, 7, 6, 5, 4, 3, 2, 1, 0, +1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 or 180 or any value or range of values therebetween in 0.1 degree increments. Note that this is for a relatively long array in the lateral wall hugging configuration. In other embodiments, the "arrow" would be at about the 6 O'clock position at the bottom of the cochlea (about where the tip is shown in FIG. 28).

In an exemplary embodiment, the distance from the X to the tip, as measured along the longitudinal axis of the electrode array (which curves in the inserted state), is about 15 mm, or about 16 mm, or about 17 mm, or about 18 mm, or about 19 mm or about 20 mm or about 21 mm. In some embodiments, the distance is between about 12 mm to about 35 mm or any value or range of values therebetween in about 0.1 mm increments.

Figure 30:
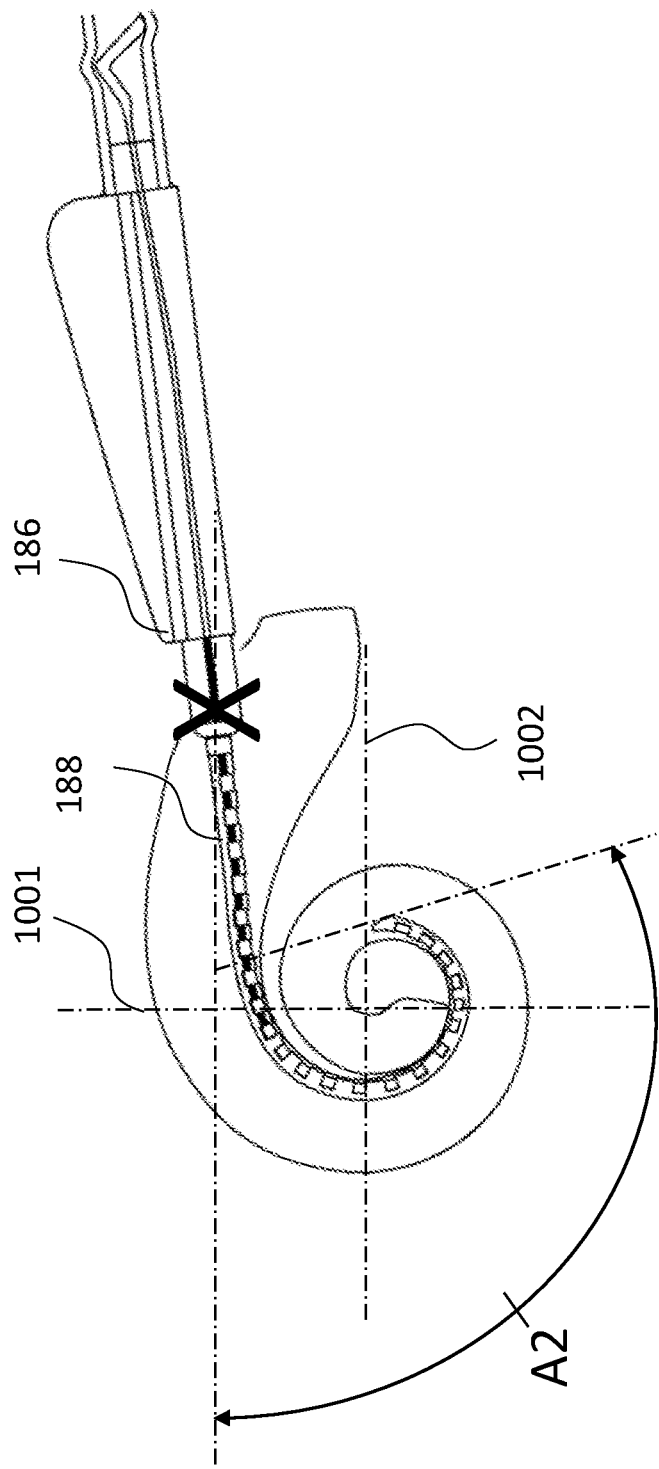

FIG. 30 depicts a modulus hugging insertion. With respect to the axis 1001 and 1002, the electrode array subtends an angle of about 270 degrees (note that the array is not parallel with the axis 1002 as shown, but can be in other embodiments). With respect to FIG. 31, which depicts another frame of reference as measured from the axis 1078 that passes through the round window 1077 (the traditional frame of reference, that of FIG. 29), where axis 1080 extends through the traditional center used to calculate insertion depth, the second insertion depth being A2B, which is about 350 degrees to about 355 degrees.

In an exemplary embodiment where the tip of the electrode array is inserted into the cochlea, the angle A2 would be about 120 degrees where the above asymmetry features would first be seen (e.g. the phenomenon of FIG. 16 would occur when the tip reached that angle). In an exemplary embodiment, A2 is about 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160 degrees, or any value or range of values therebetween in 0.1 degree increments. (Again, note that 250 degrees is added to those values—thus, A4 would be 340, 341, 342, etc.)

Figure 31:
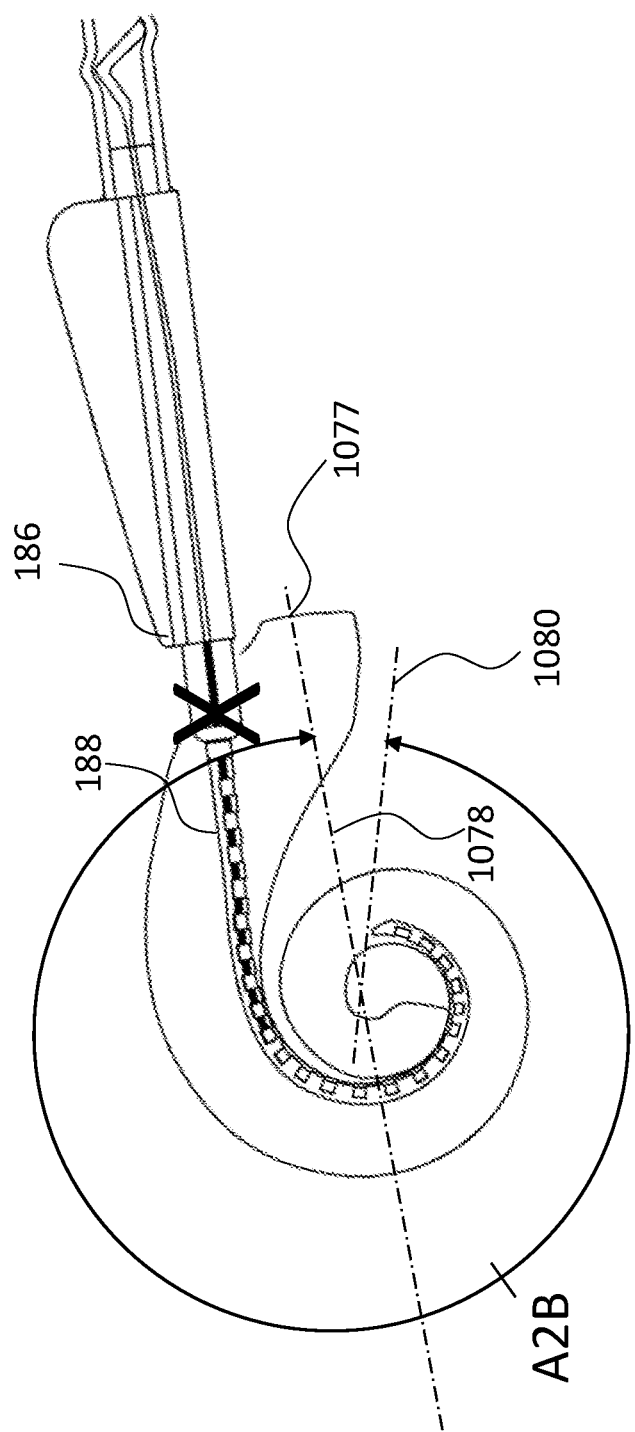

With respect to the frame of reference in FIG. 31, A2B would be about 350 degrees where the above asymmetry features would first be seen (e.g. the phenomenon of FIG. 16 would occur when the tip reached that angle). In an exemplary embodiment, A2B is about 200 degrees plus 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185 degrees, or any value or range of values therebetween in 0.1 degree increments. (Again, note that 200 degrees is added to those values—thus, A2B would be 290, 291, 292, etc.)

FIG. 31 presents an electrode array in a geometry that is about that which corresponds to the geometries of FIGS. 24 to 26. In this regard, in embodiments where FIGS. 24 to 26 and 30 and 31 are to scale, the arrangement in FIG. 31 shows the location of the electrode array where the phenomenon of FIG. 16 would first be detected.

In an exemplary embodiment, there is a method that includes executing method 2100 while also executing the action of determining that an apical end of an electrode array within the cochlea and/or an apical electrode within the cochlea is at about the Y degree insertion location based on the detected asymmetry, wherein the electrode array is part of the cochlear implant and includes the two intra-cochlea measurement electrodes. In an exemplary embodiment, Y is 230, 240, 250, 260, 270, 280, 290, 300, 310, 320, 330, 340, or any value or range of values therebetween in 1 degree increments.

Referring back to FIGS. 5-9 above, it can be seen that embodiments include systems and/or subsystems to execute the methods and/or method actions detailed herein or other pertinent method actions. To this end, there is an exemplary system, including a cochlear implant subsystem, which can correspond to the test unit 3960 detailed above, in FIG. 5, which includes an electrode array, which can correspond to electrode array 146. The system also includes a control subsystem, which can correspond to the control unit 8310 and/or with other units as detailed herein. It is noted that in this exemplary embodiment, the two subsystems are separate from each other in that they are not provided in a single unit. However, in an alternate embodiment, the two subsystems are part of a single unit, such as the implantable component 100. Note also that in an exemplary embodiment, the control subsystem can correspond to the external component of the cochlear implant system.

In an exemplary embodiment, the system is configured to operate electrodes of the electrode array as a source and a sink, operate electrodes of the electrode array as read electrodes and enable communication between the control sub-system and the cochlear implant sub-system. Further, the control sub-system is configured to evaluate signals from the cochlear implant sub-system to identify the existence of an asymmetrical electrical field about the electrode array. In an exemplary embodiment, the control subsystem can receive input from the test unit 3960 indicative of the voltages or other electrical properties that are read at the read electrodes and can make a comparison between the inputs from the respective read electrodes and, based on the comparison, determining whether or not there exists an asymmetrical field about the electrode array. In an exemplary embodiment, the system can include logic circuits and/or can include lookup tables that the system accesses to determine whether or not the data is indicative of a asymmetrical field. This can be executed utilizing hardware and/or firmware and/or software. Thus, the system can include a circuit and/or a processor and/or a microprocessor configured to analyze the data. In an exemplary embodiment, a simple exemplary algorithm could include receiving data indicative of the voltage at the first electrode utilized as a read electrode relative to the reference electrode as well as receiving data indicative of the voltage at the second electrode utilized as a read electrode relative to the reference electrode, and performing an automated evaluation that could include determining that the difference between the respective voltages and then utilizing the lookup table to determine whether or not the determined difference is greater than or less than a predetermined amount, and based on the lookup table, determine that the symmetrical field and/or an asymmetrical field exist.

In any event, in the exemplary embodiment of FIG. 5, the control sub-system is a control unit that is a separate component from the cochlear implant sub-system and in signal communication therewith via an inductance coil of the cochlear implant sub-system. In an exemplary embodiment, the control unit can be a personal computer in signal communication with an inductance coil that in turn is in signal communication with the inductance coil of the cochlear implant subsystem, wherein the personal computer receives electrical signals from its inductance coil indicative of the readings obtained by the implantable component. The personal computer can have programming residing thereon that analyzes, in an automated manner, in some embodiments, the data representative of the signals received from the inductance coil and execute one or more of the method actions detailed herein or variations thereof, such as evaluating the signals from the cochlear implant subsystem to identify the existence of the asymmetrical electric field about the electrode array and/or the presence of asymmetrical field about the electrode array. In an exemplary embodiment, the system is configured to provide an indication to a surgeon of a phenomenon associated with the electrical field. That can be provided via a buzzer, a light, a computer monitor screen, etc. It can also be provided by a voice auditory indication to the surgeon or other healthcare professional.

In an exemplary embodiment, consistent with the utilization of a computing device such as a personal computer or otherwise, a device including processing, the system is configured to repeatedly compare data from a plurality of read electrodes of the cochlear implant sub-system and identify a change in the data that indicates that the electrode array is in one or more states within the cochlea. In an exemplary embodiment, the one or more states within the cochlea can correspond to a location of the tip and/or the most distal read electrode or most distal stimulating electrode within the cochlea, where the distance from the end of the array to the closest electrode is less than 0.025, 0.05, 0.075, 0.1, 0.15, 0.2, 0.25, 0.3, 0.35, 0.4, 0.45, 0.5, 0.55, 0.6, 0.65. 0.7, 0.75, 0.8, 0.9, 1, 1.1, 1.2, 1.3, 1.4, 1.5 mm. in an exemplary embodiment, the one or more states within the cochlea can correspond to a construction were a constriction proximate the tip and/or the most apical electrode array. In an exemplary embodiment, the construction is a significant constriction and/or an abrupt construction relative to that which was the case prior to the electrode array being advanced into the cochlea such that the electric field was influenced by such construction.

In an exemplary embodiment, the construction is a constriction that constructs the maximum diameter and/or the minimum diameter of the cochlea by at least about 5, 10, 15, 20, 25, 30, 35, 35, 40, 45, 50, 55, 60, 65, 70, 75, 80, 85, 90, or 95%. In an exemplary embodiment, the aforementioned percentages of construction occur within a distance along the longitudinal direction of the cochlea of less than 0.01, 0.25, 0.05, 0.075, 0.1, 0.15, 0.2, 0.25, 0.3, 0.35, 0.4, 0.45, 0.5, 0.55, 0.6, 0.65. 0.7, 0.75, 0.8, 0.9, 1, 1.1, 1.2, 1.3, 1.4, 1.5, 1.75, 2, 2.5, 3, 3.5, 4, 4.5, 5, 5.5, 6, 7, 8, or 9 mm.

It is also noted that in an exemplary embodiment, the state can be that the tip of the electrode array and/or or more of the electrodes is located in the cochlea where the local diameter thereof is less than 1, 1.1, 1.2, 1.3, 1.4, 1.5, 1.75, 2, 2.5, 3, 3.5, 4, 4.5, or 5 mm.

In an exemplary embodiment, the state can be that the electrode array has pierced the scala of the cochlea. In an exemplary embodiment, the state can be that one or more of the electrodes of the electrode array is contacting a wall of the cochlea. In an exemplary embodiment, this can be determined based on the occurrence of one or more the phenomenon detailed herein vis-á-vis the electric field correlated to the known fact that a number of electrodes have not been inserted into the cochlea of the electrode array and/or that only a certain number of electrodes of the electrode array have been inserted into the cochlea. In this regard, in an exemplary embodiment, because the phenomenon is expected to occur at the 270° turn, if the phenomenon exists before one would expect the tip of the electrode to reach that turn, based on, the fact that the amounts of electrode array inserted into the cochlea is less than that which would otherwise be the case, such can lead to a determination that the array has punctured the wall of the cochlea. The degree of imbalance in the fields can be another example along with the pattern created, such as a constriction at the apical measurement pair followed by a constriction at the basal measurement pair.

In an exemplary embodiment, the control sub-system is a control unit that is a separate component from the cochlear implant sub-system and in signal communication therewith via an inductance coil of the cochlear implant sub-system and the system is configured to provide an indication to a surgeon of a phenomenon associated with the electrical field. In an exemplary embodiment, this can entail any of the aforementioned indicators detailed herein. In an exemplary embodiment, a computer screen can be presented that presents the voltage curves, where change in the voltage curve over time indicates the existence of the phenomenon associated with the electric field. In an exemplary embodiment, the phenomenon can be any of those detailed herein and/or variations thereof vis-á-vis the cochlea and/or the electrode array.

In an exemplary embodiment, the system is configured to provide an instruction to the surgeon to stop advancement of the electrode array into the cochlea during an implantation surgery based on a phenomenon associated with the electrical field. Again, this can be via any of the indicators detailed herein or variations thereof.

With reference to FIG. 16, it can be seen that as the electrode array is inserted into the cochlea, additional electrodes become available to be utilized as read electrodes, as those electrodes are inserted into the cochlea. Thus, in an exemplary embodiment, the system is configured to take into account additional electrodes of the electrode array as those electrodes are inserted into the cochlea during an insertion operation and compare data from the increasing number of read electrodes available with increased insertion depth to data obtained with fewer electrode(s) inserted into the cochlea, and identify the occurrence of an electrode array-cochlea structure proximity based on the comparison of the data.

In any event, consistent with the teachings detailed herein where data is repeatedly obtained from the read electrodes at different temporal locations, in an exemplary embodiment, the system is configured to repeatedly read electrical properties at various read electrodes of the electrode array and identify a rapid baseline shift in the data from the read electrodes. The system is also configured to ignore a non-rapid baseline shift in the data from the read electrodes. In an exemplary embodiment, the system is configured to identify a shift that amounts to a baseline shift that is more than 1, 2, 3, 4, 5, 6, 9, 10, 15, 20, 25, 30, 35, 35, 40, 45, 50, 55, 60, 65, 70, 75, 80, 90, 100, 125, 150, 175, or 200% within a certain temporal period and/or within a certain insertion distance or outside of any other constraints. In an exemplary embodiment, the baseline shift can be based on a percentage shift at any single location along the curve and/or can constitute the average shift of the curve (mean or median).

Consistent with the embodiments of FIGS. 22 and 23, in an exemplary embodiment, the system is configured to operate the electrode array such that at least one of:
  (i) the most apical electrode is a stimulating electrode; the next most apical electrode is a read electrode; the next most apical electrode is a reference electrode; the next most apical electrode is a read electrode; and the next most apical electrode is a stimulating electrode; or
  (ii) the most apical electrode is read electrode; the next most apical electrode is a stimulating electrode; the next most apical electrode is a reference electrode; the next most apical electrode is a stimulating electrode; and the next most apical electrode is a read electrode.

It is briefly noted that in at least some exemplary embodiments of the teachings detailed herein, by halting insertion of the electrode array upon identification of the biomarkers, such can prevent or otherwise reduce the amount of trauma that would exist or otherwise occur if the electrode array was continued to be advanced further into the cochlea. In an exemplary embodiment, such can preserve residual hearing. In an exemplary embodiment, such minimizes overlap of the electrodes in the cochlea relative to the locations where acoustic hearing remains. This can have utilitarian value with respect to so-called lateral wall insertions.

It is also noted that in at least some exemplary embodiments of the teachings detailed herein, by halting insertion of the electrode array upon identification of the biomarkers, such can prevent or otherwise avoid buckling of the electrode array. It is also noted that in an exemplary embodiment, such as in a scenario of perimodiolar insertion of the electrode array, by repeatedly taking measurements in evaluating the shape of the electric field, one can have confidence that the insertion is going well or otherwise is going as it should be as opposed to a problem developing with the insertion.

Any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, unless such is otherwise noted.

Any disclosure herein of a method of making a device herein corresponds to a disclosure of the resulting device. Any disclosure herein of a device corresponds to a disclosure of making such a device.

Any one or more elements or features disclosed herein can be specifically excluded from use with one or more or all of the other features disclosed herein.

While various embodiments of the present invention have been described above, it should be understood that they have been presented by way of example only, and not limitation. It will be apparent to persons skilled in the relevant art that various changes in form and detail can be made therein without departing from the scope of the invention.

The invention claimed is:

1. A method comprising:
   measuring a voltage, induced by an electric field, at a plurality of intra-cochlea electrodes located in a cochlea, wherein the voltages are measured relative to a common reference electrode separate from the plurality of intra-cochlea electrodes where the measurements are taken;
   monitoring the relative magnitude of the measured voltages over time; and
   detecting a voltage change across the plurality of intra-cochlea electrodes based on the monitored relative magnitude that is representative of a voltage change at the reference electrode.

2. The method of claim 1, wherein the electric field comprises an electric dipole formed by stimulating between two intra-cochlea electrodes in the cochlea.

3. The method of claim 2, wherein the reference electrode is disposed between the two stimulating intra-cochlea electrodes.

4. The method of claim 1, comprising:
   sourcing current at a first intra-cochlea electrode, and sinking current at a second intra-cochlea electrode, to create the electric field.

5. The method of claim 1, wherein the change in voltage occurs simultaneously at respective electrodes of the plurality of intra-cochlea electrodes.

6. The method of claim 1, wherein the plurality of electrodes includes at least 10 electrodes, and wherein the change in voltage occurs simultaneously at the respective electrodes of the plurality of intra-cochlea electrodes.

7. The method of claim 1, further comprising:
   inserting an electrode array into the cochlea while measuring the voltage at the plurality of electrodes; and
   halting insertion upon the detection of the voltage change, wherein
   the change in voltage occurs simultaneously at all electrodes in the cochlea where measurements are taken and occurs over an insertion distance of less than 3 mm.

8. The method of claim 1, wherein the change in voltage is the same at respective electrodes of the plurality of intra-cochlea electrodes.

9. The method of claim 1, wherein the voltage change at the reference electrode impacts all voltage measurements at the plurality of electrodes equally.

10. The method of claim 1, wherein the plurality of electrodes include at least 6 electrodes, and wherein the voltage change at the reference electrode impacts all voltage measurements at the plurality of electrodes equally.

11. The method of claim 1, wherein the voltage change is due to compression of an electrical field around an apical portion of a cochlea electrode array of which the plurality of intra-cochlea electrodes are a part.

12. The method of claim 1, wherein the plurality of electrodes includes at least 10 electrodes, and wherein the voltage change at the reference electrode impacts all voltage measurements at the plurality of electrodes equally, which change occurs simultaneously at the at least 10 respective electrodes of the plurality of intra-cochlea electrodes.

13. The method of claim 1, wherein:
   the actions of measuring a voltage, monitoring the relative magnitude and detecting the voltage are executed during a surgery implanting the intra-cochlea electrodes in the cochlea.

14. The method of claim 1, wherein:
   the action of measuring the voltage and the action of monitoring the relative magnitude and the action of detecting the voltage change are all executed while the intra-cochlear electrodes are being advanced in the cochlea.

15. The method of claim 1, further comprising:
   determining that there is a constriction in the cochlea based on the detected voltage change.

16. The method of claim 1, wherein the plurality of intra-cochlea electrodes located in the cochlea include at least four electrodes, and wherein the at least four electrodes are disposed symmetrically about the common reference electrode.

17. The method of claim 1, wherein:
   the method further includes automatically providing an instruction to a surgeon implanting the intra-cochlea electrodes based on the detected voltage change.

18. The method of claim 1, further comprising:
   during a first temporal period, pushing an electrode array into the cochlea, wherein the electrode array includes the intra-cochlea electrodes located in the cochlea; and
   during a second temporal period after the first temporal period, halting the pushing of the electrode array into the cochlea upon detecting the voltage change.

19. The method of claim 1, further comprising:
determining a biomarker based on the detected voltage change.

20. The method of claim 1, wherein:
the detected voltage change is due to a narrowing of the cochlea.

* * * * *